Figure 1:
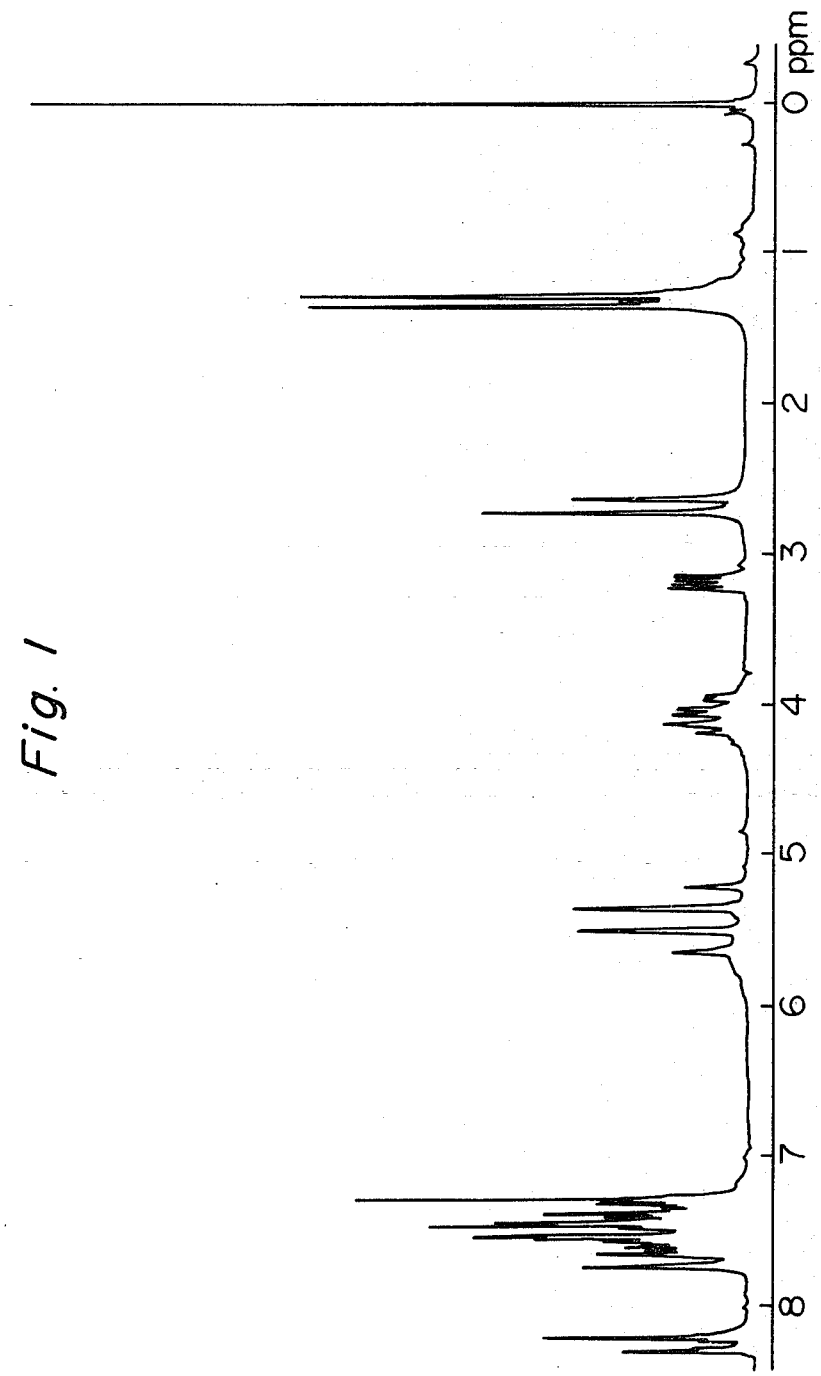

United States Patent [19]

Yoshioka et al.

[11] 4,337,199
[45] Jun. 29, 1982

[54] ANTIBIOTIC β-LACTAM COMPOUNDS, PRODUCTION THEREOF, AND THEIR USE AS ANTIMICROBIAL AGENT

[75] Inventors: Takeo Yoshioka, Ayase; Kenichi Yamamoto, Fujisawa; Kaoru Yamada, Chigasaki; Yasuyuki Kato, Kawasaki; Yasutaka Shimauchi, Ninomiya; Tomoyuki Ishikura, Chigasaki, all of Japan

[73] Assignee: Sanraku-Ocean Co., Ltd., Tokyo, Japan

[21] Appl. No.: 147,146

[22] Filed: May 6, 1980

Related U.S. Application Data

[63] Continuation-in-part of Ser. No. 90,071, Oct. 31, 1979, abandoned.

[30] Foreign Application Priority Data

Nov. 1, 1978 [JP] Japan ............................ 53-133773
Jul. 27, 1979 [JP] Japan ............................ 54-94891

[51] Int. Cl.³ .................... C07D 487/04; A61K 31/40
[52] U.S. Cl. ........................... 260/245.2 T; 546/272; 544/298; 544/316; 424/274
[58] Field of Search ................................ 260/245.2 T

[56] References Cited

U.S. PATENT DOCUMENTS

| 4,153,714 | 5/1979 | Ponsford ........................ 260/245.2 T |
| 4,162,324 | 7/1979 | Cassidy et al. ........................ 424/274 |
| 4,203,902 | 5/1980 | Sahi ............................ 260/245.2 T |
| 4,210,661 | 7/1980 | Ponsford et al. ............. 260/245.2 T |

FOREIGN PATENT DOCUMENTS

| 1567 | 5/1979 | European Pat. Off. . |
| 1627 | 5/1979 | European Pat. Off. . |
| 1628 | 5/1979 | European Pat. Off. . |
| 2813922 | 10/1978 | Fed. Rep. of Germany . |
| 54-66696 | 5/1979 | Japan . |
| 54-66697 | 5/1979 | Japan . |

*Primary Examiner*—Mark L. Berch
*Attorney, Agent, or Firm*—Wenderoth, Lind & Ponack

[57] ABSTRACT

Novel antibiotic β-lactam compounds, i.e. 7-oxo-1-azabicyclo(3.2.0)hept-2-ene-2-carboxylic acid derivatives of the following formula

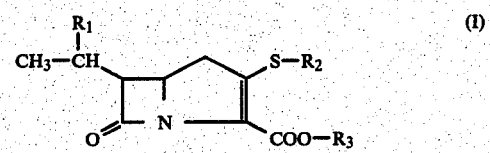

wherein
$R_1$ represents a hydrogen atom, a methyl group or a hydroxyl group,
$R_2$ represents a lower alkyl group, a hydroxy lower alkyl group, a lower alkoxy-lower alkyl group, a lower alkanoyloxy-lower alkyl group, a cyclohexyl group, a phenyl group or a 5- or 6-membered aromatic heterocyclic group containing 1 or 2 nitrogen atoms, and
$R_3$ represents a hydrogen atom, a lower alkyl group, or a substituted or unsubstituted aralkyl group containing 7 to 20 carbon atoms, and the salts thereof; processes for production thereof; use thereof as antimicrobial agents; and novel intermediates for production of the compounds of formula (I).

12 Claims, 2 Drawing Figures

ANTIBIOTIC β-LACTAM COMPOUNDS, PRODUCTION THEREOF, AND THEIR USE AS ANTIMICROBIAL AGENT

This application is a continuation-in-part of application Ser. No. 90,071, filed Oct. 31, 1979, now abandoned.

This invention relates to novel antibiotic β-lactam compounds, i.e. 7-oxo-1-azabicyclo[3.2.0]hept-2-ene-2-carboxylic acid derivatives. More specifically, this invention relates to compounds of the following formula

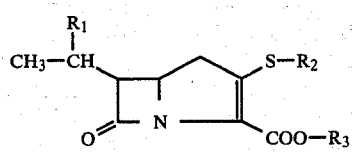

wherein
$R_1$ represents a hydrogen atom, a methyl group or a hydroxyl group,
$R_2$ represents a lower alkyl group, a hydroxy lower alkyl group, a lower alkoxy-lower alkyl group, a lower alkanoyloxy-lower alkyl group, a cyclohexyl group, a phenyl group or a 5- or 6-membered aromatic heterocyclic group containing 1 or 2 nitrogen atoms, and
$R_3$ represents a hydrogen atom, a lower alkyl group, or a substituted or unsubstituted aralkyl group containing 7 to 20 carbon atoms,
and the salts thereof; processes for production thereof; use thereof as antimicrobial agents; and to novel intermediates for production of the above compounds of formula (I).

Japanese Laid-Open Patent Publication No. 66697/79 shows compounds of the following formula

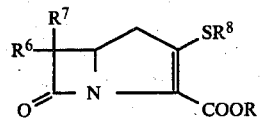

as 7-oxo-1-azabicyclo[3.2.0]hept-2-ene-2-carboxylic acid derivatives, and gives a very broad range of definition to the substituents R, $R^6$, $R^7$ and $R^8$ at the 2-, 6-, 6- and 3-positions, respectively. This Laid-Open Patent Publication gives no disclosure about the compounds of formula (I) given hereinabove and analogous compounds thereof.

The present inventors developed novel antibiotics having the structure of the following formula

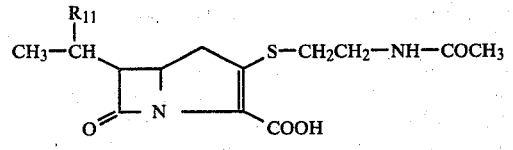

wherein $R_{11}$ represents a hydrogen atom or a methyl group,
as antibiotically active compounds isolated from the aerobic cultivation product of a microorganism, Streptomyces sp. A 271 (ATCC 31358), and named them "PS-5" [$R_{11}$=H in formula (A)] and "PS-6" $R_{11}$=CH$_3$ in formula (A)], respectively (see German Offenlegungsschrift No. 2,813,922, and European Patent Application, Published Specification No. 1567).

The present inventors further established an advantageous commercial process for producing a known compound of the following formula

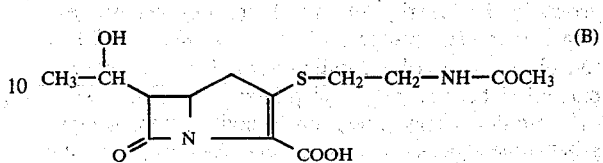

(see, for example, U.S. Pat. No. 4,162,324), and named this compound "antibiotic PS-3". They applied for a patent on this process in Japan (Japanese Patent Application No. 125053/78, laid open on Apr. 22, 1980 as Japanese Laid-Open Patent Publication No. 54899/80).

The present inventors continued their investigations in order to develop derivatives having better antimicrobial activities and/or stability than the antibiotics PS-5, PS-6 and PS-3. These investigations have led to the discovery that the β-lactam compounds of formula (I) have very good activities.

It is an object of this invention therefore to provide antibiotic β-lactam compounds of formula (I) having superior antibiotic activity and/or stability.

Another object of this invention is to provide a process for producing said antibiotic β-lactam compounds.

Still another object of this invention is to provide the use of said antibiotic β-lactam compounds as antimicrobial agents, pharmaceutical preparations comprising said β-lactam compounds as an active ingredient, and a method for preventing or treating infectious diseases caused by Gram-positive and Gram-negative bacteria by using said β-lactam compounds.

A further object of this invention is to provide novel intermediate compounds useful for the production of said antibiotic β-lactam compounds.

Other objects of this invention will become apparent from the following description.

In the present specification and the appended claims, the terms "lower" used to qualify groups or compounds means that the groups or compounds so qualified have not more than 6, preferably not more than 4, carbon atoms.

The "lower alkyl group" in formula (I) may be linear or branched, and includes, for example, methyl, ethyl, n- or iso-propyl, n-, iso-, sec- or tert-butyl, and n-pentyl. The "hydroxy lower alkyl group" includes, for example, 2-hydroxyethyl, 2-methyl-2-hydroxyethyl, 3-hydroxypropyl, and 4-hydroxybutyl. Examples of the "lower alkoxy-lower alkyl group" include 2-methoxyethyl, 2-ethoxyethyl, 2-methoxy-2-methylethyl, 3-ethoxypropyl, and 4-ethoxybutyl. Examples of the "lower alkanoyloxy-lower alkyl group" are 2-acetoxyethyl, 2-propionyloxyethyl, 2-acetoxy-2-methylethyl, 3-propionyloxypropyl, and 4-acetoxybutyl.

In formula (I), the "5- or 6-membered aromatic heterocyclic group containing 1 or 2 nitrogen atoms" includes, for example, 2-pyridyl, 3-pyridyl, 4-pyridyl, 2-pyrimidinyl, 4-pyrimidinyl, 5-pyrimidinyl, 2-pyrrolyl, 3-pyrrolyl, 2-imidazolyl, and 4-imidazolyl. Of these, pyridyl and pyrimidinyl groups are preferred.

The "substituted or unsubstituted aralkyl group containing 7 to 20 carbon atoms" in formula (I) is preferably a lower alkyl group (especially methyl or ethyl)

substituted by 1 to 3 substituted or unsubstituted phenyl groups. Examples of the substituent on the phenyl group are halogen atoms such as chlorine and bromine, lower alkyl groups such as methyl, lower alkoxy groups such as methoxy, lower haloalkyl groups such as trifluoromethyl, a nitro group, and lower alkyl sulfonyl groups such as methylsulfonyl. Preferably, the benzene ring is mono-substituted with such a substituent. Thus, specific examples of the aralkyl group for $R_3$ are benzyl, phenethyl, benzhydryl, trityl, p-nitrobenzyl, o-nitrobenzyl, p-chlorobenzyl, o-chlorobenzyl, p-fluorobenzyl, p-bromobenzyl, p-methoxybenzyl, p-methylsulfonylbenzyl, and p-trifluoromethylbenzyl. Of these, benzyl and substituted benzyl groups, particularly the p-nitrobenzyl group, are advantageous because they can be easily split off by hydrogenolysis.

A preferred group of compounds of formula (I) includes those of formula (I) in which $R_2$ represents an alkyl group having 1 to 4 carbon atoms, a hydroxyethyl group, an ethoxyethyl group, an acetyloxyethyl group, a cyclohexyl group, a phenyl group or a 5- or 6-membered aromatic heterocyclic group containing 1 or 2 nitrogen atoms. An especially preferred group of compounds within the aforesaid group includes those in which $R_2$ is a phenyl group. Another especially preferred group of compounds within the aforesaid group includes those in which $R_2$ is a 5- or 6-membered aromatic heterocyclic group containing 1 or 2 nitrogen atoms, most preferably a pyridyl or pyrimidinyl group.

Another preferred group of compounds of formula (I) includes those in which $R_3$ represents a hydrogen atom, a methyl group, a benzyl group, a p-nitrobenzyl group or a benzhydryl group. An especially preferred group of compounds within this group includes those in which $R_3$ is a hydrogen atom or a p-nitrobenzyl group.

Thus, among the compounds of formula (I) provided by this invention, preferred species are those of the following formula

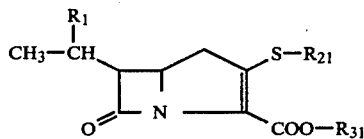

(I-a)

wherein $R_1$ is as defined hereinabove, $R_{21}$ represents an alkyl group having 1 to 4 carbon atoms, a hydroxyethyl group, an ethoxyethyl group, an acetoxyethyl group, a cyclohexyl group, a phenyl group, or a 5- or 6-membered aromatic heterocyclic group containing 1 or 2 nitrogen atoms, and $R_{31}$ represents a hydrogen atom, a methyl group, a benzyl group, a p-nitrobenzyl group or a benzhydryl group.

Especially preferred species are compounds of the following formula

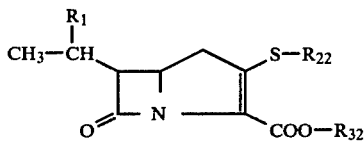

(I-b)

wherein $R_1$ is as defined hereinabove, $R_{22}$ represents a phenyl group, or a 5- or 6-membered aromatic heterocyclic group containing 1 or 2 nitrogen atoms, especially a pyridyl or pyrimidinyl group, and $R_{32}$ represents a hydrogen atom or a p-nitrobenzyl group.

Compounds of formula (I) in which $R^3$ is a hydrogen atom may be obtained in the form of a salt. Examples of such salts include alkali metal salts such as sodium, potassium or lithium salts; alkaline earth metal salts such as calcium or magnesium salts; metal salts such as aluminum salts; ammonium salts; salts of primary, secondary or tertiary amines such as monoethylamine, dimethylamine, trimethylamine, monoethanolamine or diethanolamine; and salts of other organic bases such as benzathine or procaine salts. Of these, pharmaceutically acceptable salts are preferred, and the alkali metal salts such as sodium or potassium salts are especially preferred.

The following can be cited as typical examples of the compounds of formula (I) or the salts thereof in accordance with this invention in addition to the specific compounds shown in Examples to be given hereinbelow.

benzyl 3-ethylthio-6-ethyl-7-oxo-1-azabicyclo[3.2.0-]hept-2-ene-2-carboxylate, benzhydryl 3-n-propylthio-6-ethyl-7-oxo-1-azabicyclo[3.2.0]hept-2-ene-2-carboxylate, sodium 3-(2-hydroxyethylthio)-6-ethyl-7-oxo-1-azabicylo[3.2.0]hept-2-ene-2-carboxylate, trityl 3-methoxyethylthio-6-isopropyl-7-oxo-1-azabicyclo[3.2.0]hept-2-ene-2-carboxylate, o-nitrobenzyl 3-isobutylthio-6-ethyl-7-oxo-1-azabicyclo[3.2.0]hept-2-ene-2-carboxylate, p-chlorobenzyl 5,6-trans-3-(2-acetoxyethylthio)-6-(1-hydroxyethyl)-7-oxo-1-azabicyclo[3.2.0]hept-2-ene-2-carboxylate, potassium 5,6-cis-3-isopropyl-6-(1-hydroxyethyl)-7-oxo-1-azabicyclo[3.2.0]hept-2-ene-2-carboxylate, o-chlorobenzyl 3-(2-propionyloxyethylthio)-6-ethyl-7-oxo-1-azabicyclo[3.2.0]hept-2-ene-2-carboxylate, p-fluorobenzyl 3-(2-acetoxy-2-methylethylthio)-6-isopropyl-7-oxo-1-azabicyclo[3.2.0]hept-2-ene-2-carboxylate, p-bromobenzyl 5,6-trans-3-(sec-butylthio)-6-(1-hydroxyethyl)-7-oxo-1-azabicyclo[3.2.0]hept-2-ene-2-carboxylate, p-methoxybenzyl 5,6-cis-3-(2-hydroxy-2-methylethylthio)-6-(1-hydroxyethyl)-7-oxo-1-azabicyclo[3.2.0-]hept-2-ene-2-carboxylate, lithium 5,6-trans-3-(3-hydroxypropylthio)-6-(1-hydroxyethyl)-7-oxo-1-azabicyclo[3.2.0]hept-2-ene-2-carboxylate, p-methylsulfonylbenzyl 5,6-cis-3-(2-methoxy-2-methylethylthio)-6-(1-hydroxyethyl)-7-oxo-1-azabicyclo[3.2.0]hept-2-ene-2-carboxylate, sodium 3-(4-hydroxybutylthio)-6-ethyl-7-oxo-1-azabicyclo[3.2.0]hept-2-ene-2-carboxylate, potassium 3-(n-pentylthio)-6-(1-hydroxyethyl)-7-oxo-1-azabicyclo[3.2.0]hept-2-ene-2-carboxylate, p-trifluoromethylbenzyl 3-(3-ethoxypropylthio)-6-ethyl-7-oxo-1-azabicyclo[3.2.0]hept-2-ene-2-carboxylate, benzyl 3-(tert-butylthio)-6-isopropyl-7-oxo-1-azabicyclo[3.2.0]hept-2-ene-2-carboxylate, benzhydryl 5,6-trans-3-(4-ethoxybutylthio)-6-(1-hydroxyethyl)-7-oxo-1-azabicyclo[3.2.0]hept-2-ene-2-carboxylate,
trityl 5,6-cis-3-(4-acetoxybutylthio)-6-(1-hydroxyethyl)-7-oxo-1-azabicyclo[3.2.0]hept-2-ene-2-carboxylate,
o-nitrobenzyl 3-(3-pyridylthio)-6-isopropyl-7-oxo-1-azabicyclo[3.2.0]hept-2-ene-2-carboxylate,
3-(3-pyridylthio)-6-ethyl-7-oxo-1-azabicyclo[3.2.0]hept-2-ene-2-carboxylic acid,
p-chlorobenzyl 5,6-trans-3-(3-pyridylthio)-6-(1-hydroxyethyl)-7-oxo-1-azabicyclo[3.2.0]hept-2-ene-2-carboxylate,
5,6-cis-3-(3-pyridylthio)-6-(1-hydroxyethyl)-7-oxo-1-azabicyclo[3.2.0]hept-2-ene-2-carboxylic acid,
o-chlorobenzyl 3-(4-pyrimidinylthio)-6-ethyl-7-oxo-1-azabicyclo[3.2.0]hept-2-ene-2-carboxylate,
3-(5-pyrimidinylthio)-6-isopropyl-7-oxo-1-azabicyclo[3.2.0]hept-2-ene-2-carboxylic acid,
5,6-trans-3-(4-pyrimidinylthio)-6-(1-hydroxyethyl)-7-oxo-1-azabicyclo[3.2.0]hept-2-ene-2-carboxylic acid,
p-fluorobenzyl 5,6-cis-3-(5-pyrimidinylthio)-6-(1-hydroxyethyl)-7-oxo-1-azabicyclo[3.2.0]hept-2-ene-2-carboxylate,
p-bromobenzyl 3-(2-pyrrolylthio)-6-ethyl-7-oxo-1-azabicyclo[3.2.0]hept-2-ene-2-carboxylate,
3-(3-pyrrolylthio)-6-isopropyl-7-oxo-1-azabicyclo[3.2.0]hept-2-ene-2-carboxylic acid,
p-methoxybenzyl 5,6-cis-3-(2-pyrrolylthio)-6-(1-hydroxyethyl)-7-oxo-1-azabicyclo[3.2.0]hept-2-ene-2-carboxylate,
5,6-trans-3-(3-pyrrolylthio)-6-(1-hydroxyethyl)-7-oxo-1-azabicyclo[3.2.0]hept-2-ene-2-carboxylic acid,
p-methylsulfonylbenzyl 3-(2-imidazolylthio)-6-isopropyl-7-oxo-1-azabicyclo[3.2.0]hept-2-ene-2-carboxylate,
3-(4-imidazolylthio)-6-ethyl-7-oxo-1-azabicyclo[3.2.0]hept-2-ene-2-carboxylic acid,
p-trifluoromethylbenzyl 5,6-trans-3-(2-imidazolylthio)-6-(1-hydroxyethyl)-7-oxo-1-azabicyclo[3.2.0]hept-2-ene-2-carboxylate, and
5,6-cis-3-(4-imidazolylthio)-6-(1-hydroxyethyl)-7-oxo-1-azabicyclo[3.2.0]hept-2-ene-2-carboxylic acid.

The compounds of formula (I) or the salts thereof can be produced by a process which comprises reacting a compound of the formula

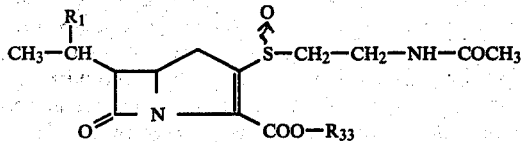

where $R_1$ is as defined hereinabove, and $R_{33}$ represents a lower alkyl group, or a substituted or unsubstituted aralkyl group having 7 to 20 carbon atoms, with a thiol compound of the following formula

wherein $R_2$ is as defined hereinabove,
or its reactive derivative, and to produce a compound of formula (I) in which $R_3$ is a hydrogen atom, hydrogenolizing the resulting compound of the following formula

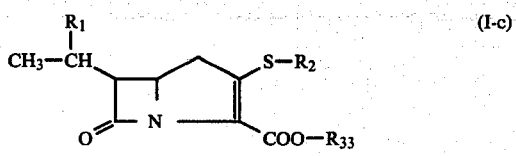

wherein $R_1$, $R_2$ and $R_{33}$ are as defined hereinabove, and if desired, converting the resulting product to its salt.

The reaction between the compound of formula (II) and the thiol compound of formula (III) or its reactive derivative is usually carried out advantageously in a solvent such as N,N-dimethylformamide (DMF), tetrahydrofuran (THF), dioxane, hexamethyl phosphoric triamide (HMPA) or glyme, especially in DMF, at a low temperature of not more than about $-20°$ C., preferably from about $-30°$ C. to about $-70°$ C. The reaction can be terminated usually within 15 minutes to 60 minutes under these conditions.

When the thiol compound of formula (III) is used, the reaction is carried out usually in the presence of a base. However, the aforesaid reaction proceeds even in the absence of a base. Examples of bases that can be used for this purpose include sodium hydride, potassium hydride, sodium amide, potassium amide, sodium hydroxide, potassium hydroxide, sodium ethoxide, sodium methoxide, potassium butoxide, triethylamine, and tripropylamine. Advantageously, the base is used in an amount of at least 0.9 equivalent, preferably 1.0 to 1.2 equivalents, per mole of the thiol compound.

Instead of using the base in the aforesaid reaction, a reactive derivative of the thiol compound of formula (III) may be used. Such reactive derivatives are preferably compounds of formula $R_2$—S—M in which M is an alkali metal. Specific examples include sodium ethanethiolate, sodium n-butanethiolate, potassium ethanethiolate, potassium propanethiolate, sodium hydroxyethanethiolate, potassium 3-hydroxypropanethiolate, sodium 2-ethoxyethanethiolate, potassium 2-methoxyethanethiolate, sodium 4-ethoxybutanethiolate, sodium 2-acetoxyethanethiolate, potassium 3-propionyloxypropanethiolate, sodium 4-pyridylthiolate, potassium 2-pyridylthiolate, sodium 3-pyridylthiolate, sodium 2-pyrimidinylthiolate, potassium 4-pyrimidinylthiolate, sodium 5-pyrimidinylthiolate, potassium 2-pyrrolylthiolate, sodium 3-pyrrolylthiolate, potassium 2-imidazolylthiolate, and sodium 4-imidazolylthiolate.

The amount of the thiol compound of formula (III) or its reactive derivative is not critical. Generally, however, it is used advantageously in an amount of at least 1.0 mole, preferably 1.1 to 1.5 moles, per mole of the compound of formula (II).

Thus, compounds of formula (1-c) are obtained.

As an alternative method, a compound of formula (I-c) in which $R_2$ is a hydroxy lower alkyl group can be converted to a compound of formula (I-c) in which $R_2$ is a lower alkanoyloxy-lower alkyl group by an acylating method known per se, for example, by reacting the former compound with a lower alkanoyl halide such as acetyl chloride or a lower alkanoic acid anhydride such as acetic anhydride.

The resulting compound of formula (I-c) can then be isolated and purified. To obtain a compound of formula (I) in which $R_3$ is a hydrogen atom, the resulting compound of formula (I-c) is hydrogenolized to split off the group $R_{33}$ and thereby to obtain a compound of the following formula

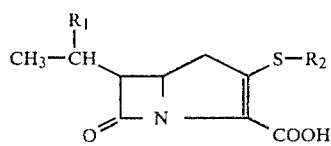 (I-d)

wherein $R_1$ and $R_2$ are as defined hereinabove.

If desired, this compound can be converted to its salt.

Isolation and purification of the compound of formula (I-c) can be performed, for example, by adding a water-immiscible inert solvent such as benzene, toluene, methylene chloride and ethyl acetate to the reaction mixture, washing the mixture with a phosphate buffer (pH 8.7) or an aqueous sodium bicarbonate solution and then with a phosphate buffer (pH 6.8), drying the solvent layer over anhydrous sodium sulfate, distilling the dried solvent layer under reduced pressure, dissolving the residue in a small amount of the aforesaid inert solvent, passing the solution through a column of Bio-Beads S-series (a styrene-divinylbenzene polymer, a product of Bio-Rad Laboratories), and developing it with the same solvent, and if required, further passing the eluate through a silica gel column. Thus, the compound of formula (I-c) can be isolated from the reaction mixture.

Hydrogenolysis of the compound of formula (I-c) can be performed in a manner know per se. For example, the compound of formula (1-c) is treated with hydrogen in a solvent such as water, and an ether such as dioxane and tetrahydrofuran in the presence of a buffer (pH at least 8) and a hydrogenation catalyst such as platinum oxide, palladium-carbon, or palladium black.

The resulting compound of formula (1-d) can be isolated usually in the form of a salt from the reaction mixture by the method described above.

The compound of formula (I) in which $R_3$ is a hydrogen atom obtained by the method described hereinabove can be converted to a salt by a conventional method, for example, by treating it with an inorganic base such as sodium bicarbonate, disodium phosphate, dipotassium phosphate, potassium 2-ethylhexanoate or ammonia, or an organic base such as monoethylamine, dimethylamine, triethylamine, monoethanolamine, diethanolamine, benzathine or procaine.

Compounds of formula (II) in which $R_1$ is a hydroxyl group are known compounds, and are described, for example, in U.S. Pat. No. 4,150,145. Compounds of formula (II) in which $R_1$ represents a hydrogen atom or a methyl group, i.e. compounds of the following formula

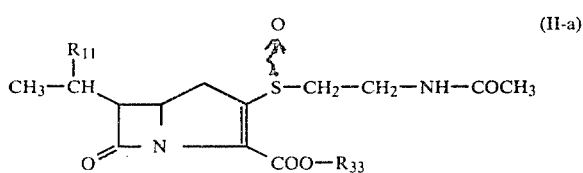 (II-a)

wherein $R_{11}$ represents a hydrogen atom or a methyl group, and $R_{33}$ is as defined hereinabove, are novel compounds. The compounds of formula (II) including the novel compounds of formula (II-a) can be prepared from the known antibiotic PS-3 of formula (B) and the antibiotics PS-5 and PS-6 of formula (A) by the same esterification method as is practiced on known carboxyl-containing antibiotics (e.g., penicillin, cephalosporin), for example, by esterification in accordance with Example 1 given hereinbelow, to form a lower alkyl ester or an unsubstituted or substituted aralkyl ester of antibiotic PS-3, PS-5 or PS-6 having the formula

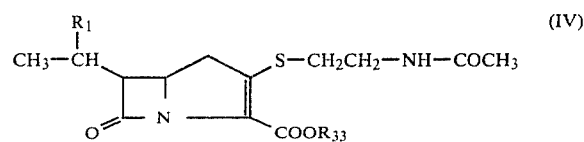 (IV)

wherein $R_1$ and $R_{33}$ are as defined hereinabove, followed by S-oxidation of the compound of formula (IV).

S-oxidation of the compound of formula (IV) can be performed by a method known per se, for example, by methods frequently utilized in the S-oxidation of sulfur-containing $\beta$-lactam antibiotics of the penicillin or cephalosporin series.

For example, the compound of formula (IV) is reacted with a mild oxidizing agent which does not substantially act on the 7-oxo-1-azabicyclo-[3.2.0]hept-2-ene-carboxylic acid skeleton, e.g. perbenzoic acid, phenyl dichloroiodide, or sodium metaperiodate. Suitable mild oxidizing agents are organic acids, especially perbenzoic acid and m-chloroperbenzoic acid. Substituted perbenzoic acids such as m-chloroperbenzoic acid are most preferred.

The reaction between the compound of formula (IV) and the oxidizing agent is carried out advantageously in an inert solvent such as methylene chloride, chloroform or carbon tetrachloride at room temperature or at a lower temperature, preferably about $-30°$ C. to about $20°$ C. The reaction can be completed under these conditions usually within 3 minutes to 3 hours.

The amount of the oxidizing agent used in the S-oxidation of the compound of formula (IV) can be varied widely depending upon the type of the oxidizing agent, the reaction conditions, etc. Generally, the advantageous amount of the oxidizing agent is 0.3 to 1.8 molar equivalents, preferably 0.7 to 1.3 molar equivalents, per mole of the compound of formula (IV).

After the reaction, the compound of formula (II), which is an S-oxidation product, can be isolated and purified by various methods known per se. Usually, this compound can be isolated from the reaction mixture by methods frequently utilized in the isolation and purification of carboxyl-containing antibiotics. Furthermore, the compound of formula (II) can be used in the aforesaid reaction without isolation and purification.

The compound of formula (II) can be isolated and purified, for example, by the following processes: The reaction mixture is diluted in the presence or absence of amines such as triethylamine or pyridine with a less polar organic solvent substantially water immiscible with water such as ethyl acetate, benzene or chloroform and then washed with a pH 6.0-8.0 buffer or 4% sodium bicarbonate aqueous solution, followed by washing again with neutral buffer or brine. After drying the solvent layer over anhydrous sodium sulfate, the compound of formula (II) can be isolated by known methods, such as for example, gel filtration using Bio-Beads S-X3 (Bio-Rad Laboratories), Sephadex LH-20 (Pharmacia Fine Chemicals AB), or the like; or adsorption chromatography using a carrier such as silica gel, alumina, fuller's earth (Froridin Co.) or the like, which can be used in some adequate combination and used repeatedly, if necessary.

Specific examples of the novel compounds of formula (II-a) are listed below.

benzyl 3-(2-acetamidethylsulfinyl)-6-ethyl-7-oxo-1-azabicyclo[3.2.0]hept-2-ene-2-carboxylate,
p-nitrobenzyl 3-(2-acetamidethylsulfinyl)-6-ethyl-7-oxo-1-azabicyclo[3.2.0]hept-2-ene-2-carboxylate,
o-nitrobenzyl 3-(2-acetamidethylsulfinyl)-6-ethyl-7-oxo-1-azabicyclo[3.2.0]hept-2-ene-2-carboxylate,
p-chlorobenzyl 3-(2-acetamidethylsulfinyl)-6-ethyl-7-oxo-1-azabicyclo[3.2.0]hept-2-ene-2-carboxylate,
p-fluorobenzyl 3-(2-acetamidethylsulfinyl)-6-ethyl-7-oxo-1-azabicyclo[3.2.0]hept-2-ene-2-carboxylate,
p-methylsulfonylbenzyl 3-(2-acetamidethylsulfinyl)-6-ethyl-7-oxo-1-azabicyclo[3.2.0]-hept 2-ene-2-carboxylate,
benzhydryl 3-(2-acetamidethylsulfinyl)-6-ethyl-7-oxo-1-azabicyclo[3.2.0]hept-2-ene-2-carboxylate,
methyl 3-(2-acetamidethylsulfinyl)-6-ethyl-7-oxo-1-azabicyclo[3.2.0]hept-2-ene-2-carboxylate,
tert.-butyl 3-(2-acetamidethylsulfinyl)-6-ethyl-7-oxo-1-azabicyclo[3.2.0]hept-2n2-2-carboxylate,
benzyl 3-(2-acetamidethylsulfinyl)-6-isopropyl-7-oxo-1-azabicyclo[3.2.0]hept-2-ene-2-carboxylate,
p-nitrobenzyl 3-(2-acetamidethylsulfinyl)-6-isopropyl-7-oxo-1-azabicyclo[3.2.0]hept-2-ene-2-carboxylate,
o-nitrobenzyl 3-(2-acetamidethylsulfinyl)-6-isopropyl-7-oxo-1-azabicyclo[3.2.0]hept-2-ene-2-carboxylate,
p-chlorobenzyl 3-(2-acetamidethylsulfinyl)-6-isopropyl-7-oxo-1-azabicyclo[3.2.0]hept-2-ene-2-carboxylate,
p-fluorobenzyl 3-(2-acetamidethylsulfinyl)-6-isopropyl-7-oxo-1-azabicyclo[3.2.0]hept-2-ene-2-carboxylate,
p-methylsulfonylbenzyl 3-(2-acetamidethylsulfinyl)-6-isopropyl-7-oxo-1-azabicyclo[3.2.0]hept-2-ene-2-carboxylate,
benzhydryl 3-(2-acetamidethylsulfinyl)-6-isopropyl-7-oxo-1-azabicyclo[3.2.0]hept-2-ene-2-carboxylate,
methyl 3-(2-acetamidethylsulfinyl)-6-isopropyl-7-oxo-1-azabicyclo[3.2.0]hept-2-ene-2-carboxylate, and
tert.-butyl 3-(2-acetamidethylsulfinyl)-6-isopropyl-7-oxo-1-azabicyclo[3.2.0]hept-2-ene-2-carboxylate.

The starting materials for the production of the compounds of formula (II) can be produced as follows:

The antibiotic PS-3 can be produced by the method described in Japanese Patent Application No. 125053/78 or U.S. Patent No. 4,162,324. The antibiotic PS-5 can be produced by the method described in J. Antibiotics, 31, 480–482 (1978) or German Offenlegungsschrift No. 2,813,922. The antibiotic PS-6 can be produced by the method described in European Patent Application Published Specification No. 1,567. Alternatively, the antibiotics PS-3, PS-5 and PS-6 can be recovered from the aerobic cultivation product of Streptomyces sp. A271 (ATCC 31358).

It has been confirmed that the antibiotic PS-3 obtained by a fermentative method has 5,6-trans and 5,6-cis steric configurations represented by the following formulae.

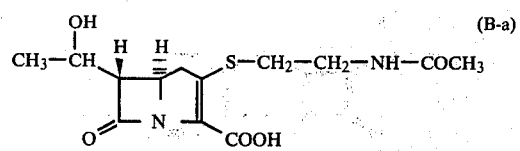

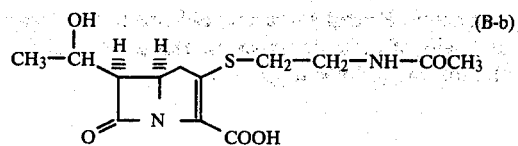

Thus, the compound of formula (I) of this invention derived from this antibiotic PS-3 may have steric configurations of the following formulae corresponding to the compounds of formulae (B-a) and (B-b).

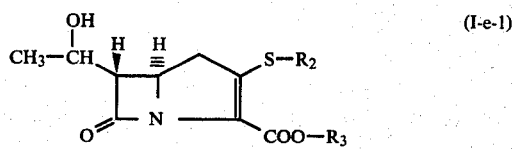

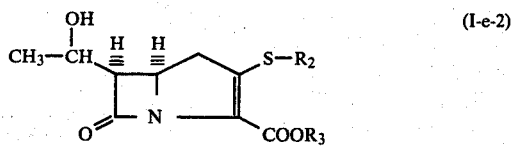

wherein $R_2$ and $R_3$ are as defined hereinabove.

It has also been confirmed that the antibiotics PS-5 and PS-6 obtained by a fermentative method usually have a 5,6-trans steric configuration of the following formula (A-a)

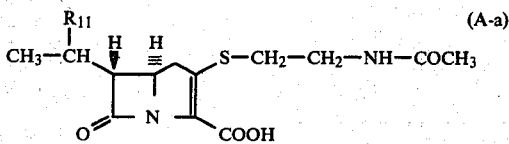

wherein $R_{11}$ is as defined hereinabove.

The compound of formula (I) of this invention derived from the antibiotics PS-5 or PS-6 having this steric configuration has a 5,6-trans steric configuration of the following formula (I e-3)

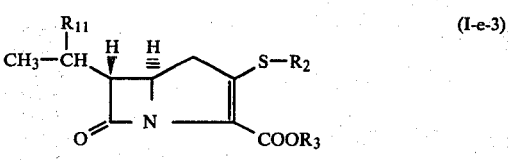

wherein $R_{11}$, $R_2$ and $R_3$ are as defined above, corresponding to the 5,6-trans configuration of PS-5 or PS-6.

It should be understood therefore that the compounds of formula (I) provided by this invention embrace those having 5,6-trans and 5,6-cis steric configurations.

The compounds of formula (I) provided by this invention, preferably the compounds of formula (1-d), especially compounds of the following formula (I-a-1)

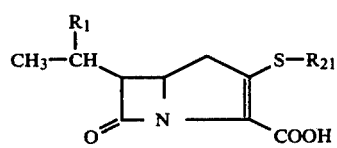

(I-a-1)

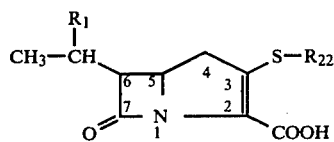

(I-b-1)

wherein $R_1$ and $R_{21}$ are as defined hereinabove, and salts of these compounds, above all compounds of the following formula (I-b-1)

wherein $R_1$ and $R_{22}$ are as defined hereinabove, and salts of these compounds have very good antimicrobial activity. This high antimicrobial activity can be confirmed by a bioassay method using *Comamonas terrigena* B-996.

Typical species of the compounds of formula (I-a-1) and (I-b-1) and their salts provided by this invention have antibiotic activities shown in Tables I-1 to I-7 below. Table I-8 shows the antibiotic activities of known compounds.

TABLE I-1

| | A compound of formula (I-b-1) | | | |
|---|---|---|---|---|
| | Antibiotic Activity minimum inhibitory concentration (μg/ml) | | | |
| | $R_1$ | | | |
| | H | —$CH_3$ | —OH* | —OH** |
| $R_{22}$ | | | | |
| Test Organism | 4-pyridyl | 4-pyridyl | 4-pyridyl | 4-pyridyl |
| *Bacillus subtilis* ATCC 6633 | <0.007 | 0.013 | 0.20 | <0.007 |
| *Sarcina lutea* | <0.007 | 0.013 | 0.10 | <0.007 |
| *Staphylococcus aureus* FDA 209P | <0.007 | 0.007 | 0.10 | <0.007 |
| *Staphylococcus aureus* Smith | <0.007 | 0.013 | 0.20 | <0.007 |
| *Staphylococcus aureus* Russell | <0.007 | 0.013 | 0.20 | <0.007 |
| *Staphylococcus epidermidis* | <0.007 | 0.013 | 0.20 | <0.007 |
| *Alcaligenes faecalis* A 1 | <0.007 | 0.013 | 0.025 | <0.007 |
| *Citrobacter freundii* GN 346 | 29.5 | 50 | 100 | 6.25 |
| *Comamonas terrigena* B-996 | <0.007 | 0.007 | 0.013 | <0.007 |
| *Enterobacter aerogenes* E19 | 7.4 | 12.5 | 50 | 1.56 |
| *Enterobacter cloacae* 45 | 29.5 | 50 | 50 | 6.25 |
| *Enterobacter* sp. E8 | 0.46 | 1.56 | 0.78 | 0.025 |
| *Escherichia coli* K-12 | 0.92 | 3.13 | 1.56 | 0.05 |
| *Escherichia coli* RGN 823 | 14.8 | 12.5 | 25 | 6.25 |
| *Klebsiella pneumoniae* K-13 | 14.8 | 25 | 25 | 25 |
| *Proteus mirabilis* P6 | 1.8 | 3.13 | 6.25 | 0.39 |
| *Proteus rettgeri* P7 | 1.8 | 1.56 | 6.25 | 0.78 |
| *Proteus vulgaris* GN76 | 29.5 | 50 | 50 | 50 |
| *Proteus* sp. P22 | 29.5 | 50 | 50 | 50 |
| *Providencia* sp. P8 | 0.92 | 3.13 | 1.56 | 0.20 |
| *Pseudomonas aeruginosa* IFO3445 | 0.92 | 1.56 | 1.56 | 1.56 |
| *Pseudomonas aeruginosa* NCTC10490 | 0.92 | 1.56 | 1.56 | 1.56 |
| *Serratia marcescens* S18 | 29.5 | 50 | 100 | 50 |
| *Serratia* | | | | |

TABLE I-1-continued

A compound of formula (I-b-1)

Antibiotic Activity
minimum inhibitory concentration
(μg/ml)

| Test Organism | $R_1$ H, $R_{22}$ pyridyl | $R_1$ —CH$_3$, $R_{22}$ pyridyl | $R_1$ —OH*, $R_{22}$ pyridyl | $R_1$ —OH**, $R_{22}$ pyridyl |
|---|---|---|---|---|
| marcescens T55 | 29.5 | 100 | 100 | 25 |

TABLE I-2

A compound of formula (I-b-1)

Antibiotic Activity
minimum inhibitory concentration
(μg/ml)

| Test Organism | $R_1$ H, $R_{22}$ pyridyl | $R_1$ —CH$_3$, $R_{22}$ pyridyl | $R_1$ —OH*, $R_{22}$ pyridyl | $R_1$ —OH**, $R_{22}$ pyridyl |
|---|---|---|---|---|
| Bacillus subtilis ATCC 6633 | 0.012 | 0.05 | 0.78 | <0.007 |
| Sarcina lutea | 0.0008 | 0.004 | 0.013 | <0.007 |
| Staphylococcus aureus FDA 209P | 0.006 | 0.007 | 0.05 | <0.007 |
| Staphylococcus aureus Smith | 0.012 | 0.013 | 0.39 | 0.013 |
| Staphylococcus aureus Russell | 0.012 | 0.013 | 0.39 | 0.013 |
| Staphylococcus epidermidis | 0.012 | 0.05 | 1.56 | 0.05 |
| Alcaligenes faecalis A 1 | 0.1 | 0.20 | 0.78 | 6.25 |
| Citrobacter freundii GN 346 | 25 | 50 | 100 | 6.25 |
| Comamonas terrigena B-996 | 0.003 | 0.007 | 0.20 | <0.007 |
| Enterobacter aerogenes E19 | 25 | 50 | >100 | 6.25 |
| Enterobacter cloacae 45 | 50 | >100 | 100 | 12.5 |
| Enterobacter sp. E8 | 12.5 | 25 | 25 | 0.78 |
| Escherichia coli K-12 | 6.25 | 12.5 | 6.25 | 0.39 |
| Escherichia coli RGN 823 | 6.25 | 12.5 | 12.5 | 3.13 |
| Klebsiella pneumoniae K-13 | 25 | 50 | 50 | 25 |
| Proteus mirabilis P6 | 3.13 | 6.25 | 12.5 | 0.39 |
| Proteus rettgeri P7 | 6.25 | 6.25 | 25 | 3.13 |
| Proteus vulgaris GN 76 | 12.5 | 12.5 | 25 | 12.5 |
| Proteus sp. P22 | 6.25 | 12.5 | 12.5 | 12.5 |
| Providencia sp. P8 | 1.56 | 3.13 | 3.13 | 0.20 |
| Pseudomonas aeruginosa IFO 3445 | 12.5 | 50 | 12.5 | 12.5 |
| Pseudomonas aeruginosa NCTC 10490 | 25 | 50 | 25 | 50 |
| Serratia marcescens S18 | 12.5 | 50 | 50 | 12.5 |
| Serratia marcescens T55 | 25 | 50 | 100 | 25 |

TABLE I-3

A compound of formula (I-b-1)
Antibiotic Activity
minimum inhibitory concentration
(μg/ml)

| Test Organism | $R_1$ H / $R_{22}$ N-N | —CH$_3$ / N-N | —OH* / N-N | —OH** / N-N |
|---|---|---|---|---|
| Bacillus subtilis ATCC 6633 | <0.012 | 0.013 | 0.39 | <0.007 |
| Sarcina lutea | <0.012 | 0.013 | 0.20 | <0.007 |
| Staphylococcus aureus FDA209P | <0.012 | 0.007 | 0.20 | <0.007 |
| Staphylococcus aureus Smith | 0.024 | 0.025 | 0.39 | 0.025 |
| Staphylococcus aureus Russell | <0.012 | 0.013 | 0.39 | 0.013 |
| Staphylococcus epidermidis | 0.024 | 0.05 | 0.39 | 0.025 |
| Alcaligenes faecalis A 1 | 0.2 | 0.39 | 1.56 | 0.05 |
| Citrobacter freundii GN 346 | 25 | 50 | 100 | 6.25 |
| Comamonas terrigena B-996 | <0.012 | 0.013 | 0.05 | <0.007 |
| Enterobacter aerogenes E19 | 12.5 | >100 | 100 | 3.13 |
| Enterobacter cloacae 45 | 25 | >100 | 50 | 12.5 |
| Enterobacter sp. E8 | 3.13 | 12.5 | 6.25 | 0.013 |
| Escherichia coli K-12 | 1.56 | 6.25 | 1.56 | 0.1 |
| Escherichia coli RGN 823 | 3.13 | 3.13 | 3.13 | 1.56 |
| Klebsiella pneumoniae K-13 | 12.5 | 25 | 25 | 25 |
| Proteus mirabilis P6 | 3.13 | 3.13 | 12.5 | 0.78 |
| Proteus rettgeri P7 | 3.13 | 3.13 | 12.5 | 1.56 |
| Proteus vulgaris GN76 | 6.25 | 12.5 | 12.5 | 6.25 |
| Proteus sp. P22 | 12.5 | 12.5 | 12.5 | 25 |
| Providencia sp. P8 | 0.78 | 1.56 | 0.78 | 0.20 |
| Pseudomonas aeruginosa IFO3445 | 12.5 | 25 | 12.5 | 25 |
| Pseudomonas aeruginosa NCTC10490 | 12.5 | 25 | 12.5 | 25 |
| Serratia marcescens S18 | 12.5 | 25 | 50 | 12.5 |
| Serratia marcescens T55 | 25 | >100 | 100 | 12.5 |

TABLE I-4

A compound of formula (I-a-1)
Antibiotic Activity
minimum inhibitory concentration
(μg/ml)

| Test Organism | $R_1$ H / $R_{21}$ ⟨H⟩ | —CH$_3$ / ⟨H⟩ | —CH* / ⟨H⟩ | —OH** / ⟨H⟩ |
|---|---|---|---|---|
| Bacillus subtilis ATCC 6633 | 0.09 | 0.20 | 6.25 | 0.013 |
| Sarcina lutea | <0.01 | 0.025 | 0.05 | <0.007 |
| Staphylococcus aureus FDA209P | <0.01 | 0.025 | 0.05 | 0.013 |

TABLE I-4-continued

A compound of formula (I-a-1)
Antibiotic Activity
minimum inhibitory concentration
(μg/ml)

| Test Organism | R₁ = H, R₂₁ = phenyl(H) | —CH₃, phenyl(H) | —CH*, phenyl(H) | —OH**, phenyl(H) |
|---|---|---|---|---|
| *Staphylococcus aureus* Smith | 0.04 | 0.05 | 0.39 | 0.05 |
| *Staphylococcus aureus* Russell | <0.01 | 0.025 | 0.20 | 0.013 |
| *Staphylococcus epidermidis* | 0.04 | 0.05 | 0.39 | 0.05 |
| *Alcaligenes faecalis* A 1 | 5.6 | 6.25 | 25 | 1.56 |
| *Citrobacter freundii* GN346 | >180 | >100 | >100 | 100 |
| *Comamonas terrigena* B-996 | <0.01 | 0.007 | 0.05 | <0.007 |
| *Enterobacter aerogenes* E19 | >180 | >100 | >100 | 50 |
| *Enterobacter cloacae* 45 | >180 | >100 | >100 | 50 |
| *Enterobacter* sp. E8 | >180 | >100 | >100 | 12.5 |
| *Escherichia coli* K-12 | 180 | >100 | >100 | 12.5 |
| *Escherichia coli* RGN 823 | 180 | >100 | >100 | 100 |
| *Klebsiella pneumoniae* K-13 | >180 | >100 | >100 | >100 |
| *Proteus mirabilis* P6 | 45 | 100 | 100 | 6.25 |
| *Proteus rettgeri* P7 | 180 | >100 | >100 | 100 |
| *Proteus vulgaris* GN76 | 180 | >100 | >100 | >100 |
| *Proteus* sp. P22 | 90 | 100 | >100 | >100 |
| *Providencia* sp. P8 | 180 | >100 | >100 | 25 |
| *Pseudomonas aeruginosa* IFO3445 | 180 | >100 | >100 | >100 |
| *Pseudomonas aeruginosa* NCTC10490 | 22.5 | 50 | 25 | 50 |
| *Serratia marcescens* S18 | >180 | >100 | >100 | >100 |
| *Serratia marcescens* T55 | >180 | >100 | >100 | >100 |

TABLE I-5

A compound of formula (I-b-1)
Antibiotic Activity
minimum inhibitory concentration
(μg/ml)

| Test Organism | R₁ = H, R₂₂ = phenyl | —CH₃ | —OH* | —OH** |
|---|---|---|---|---|
| *Bacillus subtilis* ATCC 6633 | 0.07 | 0.10 | 6.25 | 0.013 |
| *Sarcina lutea* | <0.01 | 0.013 | 0.05 | <0.007 |
| *Staphylococcus aureus* FDA209P | <0.01 | 0.013 | 0.05 | <0.007 |
| *Staphylococcus aureus* Smith | 0.1 | 0.2 | 1.56 | 0.10 |
| *Staphylococcus aureus* Russell | <0.01 | 0.025 | 0.78 | 0.013 |
| *Staphylococcus epidermidis* | <0.01 | 0.025 | 0.39 | 0.013 |
| *Alcaligenes faecalis* A1 | 4.7 | 6.25 | 25 | 1.56 |
| *Citrobacter freundii* GN346 | 150 | >100 | >100 | 100 |
| *Comamonas terrigena* B-996 | <0.01 | 0.007 | 0.05 | <0.007 |
| *Enterobacter aerogenes* E19 | 150 | >100 | >100 | 12.5 |
| *Enterobacter cloacae* 45 | 150 | >100 | >100 | 12.5 |
| *Enterobacter* sp. E8 | 75 | >100 | 100 | 3.13 |
| *Escherichia* | | | | |

TABLE I-5-continued

A compound of formula (I-b-1)

Antibiotic Activity
minimum inhibitory concentration
($\mu$g/ml)

| | $R_1$ | | | |
|---|---|---|---|---|
| | H | —$CH_3$ | —OH* | —OH** |
| Test Organism | $R_{22}$ —⟨phenyl⟩ | —⟨phenyl⟩ | —⟨phenyl⟩ | —⟨phenyl⟩ |
| Escherichia coli K-12 | 37.5 | 50 | 50 | 3.13 |
| Escherichia coli RGN823 | 37.5 | 50 | 50 | 25 |
| Klebsiella pneumoniae K-13 | >150 | >100 | >100 | >100 |
| Proteus mirabilis P6 | 75 | >100 | 100 | 12.5 |
| Proteus rettgeri P7 | 75 | 100 | >100 | 100 |
| Proteus vulgaris GN76 | 150 | >100 | >100 | >100 |
| Providencia sp. P22 | 75 | 100 | >100 | >100 |
| Pseudomonas sp. P8 | 18.8 | 25 | 50 | 3.13 |
| Pseudomonas aeruginosa IFO3445 | 18.8 | 25 | 25 | 50 |
| Pseudomonas aeruginosa NCTC10490 | 4.7 | 6.25 | 6.25 | 50 |
| Serratia marcescens S18 | 75 | >100 | >100 | 100 |
| Serratia marcescens T55 | 150 | >100 | >100 | 100 |

TABLE I-6

A compound of formula (I-a-1)

Antibiotic Activity
minimum inhibitory concentration
($\mu$g/ml)

| | $R_1$ | | | |
|---|---|---|---|---|
| | H | —$CH_3$ | —OH* | —OH** |
| Test Organism | $R_{21}$ —$CH_2CH_2OH$ | —$CH_2CH_2OH$ | —$CH_2CH_2OH$ | —$CH_2CH_2OH$ |
| Bacillus subtilis ATCC 6633 | 0.1 | 0.39 | 6.25 | 0.013 |
| Sarcina lutea | 0.1 | 0.39 | 1.56 | 0.013 |
| Staphylococcus aureus FDA209P | 0.05 | 0.20 | 0.39 | 0.013 |
| Staphylococcus aureus Smith | 0.1 | 0.39 | 3.13 | 0.10 |
| Staphylococcus aureus Russell | 0.2 | 0.39 | 3.13 | 0.20 |
| Staphylococcus epidermidis | 0.2 | 0.39 | 3.13 | 0.20 |
| Alcaligenes faecalis A 1 | 1.56 | 1.56 | 6.25 | 0.39 |
| Citrobacter freundii GN346 | 3.13 | 12.5 | 12.5 | 0.78 |
| Comamonas terrigena B-996 | 0.025 | 0.05 | 0.10 | 0.013 |
| Enterobacter aerogenes E19 | 3.13 | 12.5 | 12.5 | 0.39 |
| Enterobacter cloacae 45 | 6.25 | 25 | 6.25 | 1.56 |
| Enterobacter sp. E 8 | 3.13 | 12.5 | 6.25 | 0.20 |
| Escherichia coli K-12 | 3.13 | 12.5 | 3.13 | 0.20 |
| Escherichia coli RGN823 | 12.5 | 12.5 | 12.5 | 6.25 |
| Klebsiella pneumoniae K-13 | 12.5 | 12.5 | 25 | 25 |
| Proteus mirabilis P6 | 12.5 | 25 | 50 | 3.13 |
| Proteus rettgeri P7 | 12.5 | 12.5 | 50 | 6.25 |
| Proteus vulgaris GN76 | 25 | 25 | 50 | 25 |
| Proteus sp. P22 | 50 | 50 | 100 | 100 |
| Providencia sp. P8 | 3.13 | 6.25 | 6.25 | 0.78 |
| Pseudomonas aeruginosa IFO 3445 | 12.5 | 12.5 | 12.5 | 25 |
| Pseudomonas aeruginosa NCTC 10490 | 12.5 | 25 | 12.5 | 25 |

TABLE I-6-continued

A compound of formula (I-a-1)
Antibiotic Activity
minimum inhibitory concentration
(μg/ml)

| | $R_1$ | | | |
|---|---|---|---|---|
| | H | —$CH_3$ | —OH* | —OH** |
| | | $R_{21}$ | | |
| Test Organism | —$CH_2CH_2OH$ | —$CH_2CH_2OH$ | —$CH_2CH_2OH$ | —$CH_2CH_2OH$ |
| *Serratia marcescens* S18 | 6.25 | 12.5 | 25 | 12.5 |
| *Serratia marcescens* T55 | 12.5 | 50 | 50 | 12.5 |

TABLE I-7

A compound of formula (I-a-1)
Antibiotic Activity
Minimum Inhibitory Concentration
(μg/ml)

| | $R_1$ | |
|---|---|---|
| | H | —$CH_3$ |
| | $R_{21}$ | |
| Test Organism | $(CH_2)_3CH_3$ | $(CH_2)_3CH_3$ |
| *Bacillus subtilis* ATCC 6633 | 3.75 | 15 |
| *Sarcina lutea* | 1.88 | 7.5 |
| *Staphylococcus aureus* FDA209P | 0.24 | 0.48 |
| *Staphylococcus aureus* Smith | — | — |
| *Staphylococcus aureus* Russell | — | — |
| *Staphylococcus epidermidis* | 0.12 | 0.12 |
| *Alcaligenes faecalis* B326 | 15.0 | 20.0 |
| *Citrobacter freundii* GN346 | — | — |
| *Comamonas terrigena* B-996 | 0.24 | 0.48 |

TABLE I-8

Antibiotic Activity
Minimum Inhibitory Concentration
(μg/ml)

| Known compound Test Organism | PS-5 | PS-6 | PS-3A* | PS-3B** | CEZ |
|---|---|---|---|---|---|
| *Bacillus subtilis* ATCC 6633 | 0.10 | 0.78 | 1.25 | 0.004 | 0.20 |
| *Sarcina lutea* | 0.05 | 0.39 | 0.63 | 0.004 | 0.39 |
| *Staphylococcus aureus* FDA209P | 0.025 | 0.10 | 0.31 | 0.07 | 0.10 |
| *Staphylococcus aureus* Smith | 0.10 | 0.20 | 1.25 | 0.13 | 0.20 |
| *Staphylococcus aureus* Russell | 0.10 | 0.20 | 1.25 | 0.13 | 0.20 |
| *Staphylococcus epidermidis* | 0.10 | 0.39 | 2.5 | 0.07 | 0.10 |
| *Alcaligenes faecalis* A 1 | 0.39 | 1.56 | 1.25 | 0.07 | 3.13 |
| *Citrobacter freundii* GN346 | 3.13 | 12.5 | 10.0 | 0.53 | >200 |
| *Comamonas terrigena* B-996 | 0.013 | 0.10 | 0.08 | 0.001 | 0.20 |
| *Enterobacter aerogenes* E19 | 3.13 | 25 | 20.1 | 0.27 | >200 |
| *Enterobacter cloacae* 45 | 6.25 | 25 | 10.0 | 1.06 | >200 |
| *Enterobacter* sp. E8 | 1.56 | 6.25 | 5.0 | 0.07 | 3.13 |
| *Escherichia coli* K-12 | 1.56 | 6.25 | 2.5 | 0.07 | 1.56 |
| *Escherichia coli* RGN823 | 3.13 | 6.25 | 5.0 | 1.06 | 200 |
| *Klebsiella pneumoniae* K-13 | 6.25 | 25.0 | 10.0 | 8.5 | 200 |
| *Proteus mirabilis* P6 | 6.25 | 12.5 | 20.1 | 0.53 | 6.25 |
| *Proteus rettgeri* P7 | 12.5 | 6.25 | 20.1 | 17.0 | >200 |
| *Proteus vulgaris* GN76 | 12.5 | 12.5 | 20.1 | 8.5 | >200 |
| *Proteus* sp. P22 | 25 | 25 | 20.1 | 17.0 | >200 |
| *Providencia* sp. P8 | 3.13 | 6.25 | 5.0 | 0.27 | 100 |
| *Pseudomonas aeruginosa* IF03445 | 25 | 50 | 20.1 | 17.0 | >200 |
| *Pseudomonas aeruginosa* NCTC 10490 | 12.5 | 50 | 20.1 | 34.0 | >200 |
| *Serratia marcescens* S18 | 6.25 | 25 | 10.0 | 2.13 | >200 |
| *Serratia marcescens* T55 | 6.25 | 50 | 20.1 | 2.13 | >200 |

*5,6-trans isomer
**5,6-cis isomer

PS-5:

$$\text{CH}_3-\text{CH}_2 \diagdown \quad \diagup \text{S}-\text{CH}_2-\text{CH}_2-\text{NHCOCH}_3$$

(β-lactam structure with COOH)

PS-6:

$$\text{CH}_3 \diagdown \text{CH} \diagdown \quad \diagup \text{S}-\text{CH}_2-\text{CH}_2-\text{NHCOCH}_3$$
$$\text{CH}_3 \diagup$$

(β-lactam structure with COOH)

PS-3A:

$$\text{CH}_3-\text{CH} \overset{H}{\underset{}{\diagup}} \quad \diagup \text{S}-\text{CH}_2-\text{CH}_2-\text{NH}-\text{COCH}_3$$
$$\text{HO} \diagup$$

(β-lactam structure with COOH)

PS-3B:

$$\text{CH}_3-\text{CH} \overset{H}{\underset{}{\diagup}} \quad \diagup \text{S}-\text{CH}_2-\text{CH}_2-\text{NH}-\text{COCH}_3$$
$$\text{HO} \diagup$$

(β-lactam structure with COOH)

CEZ (cephazolin):

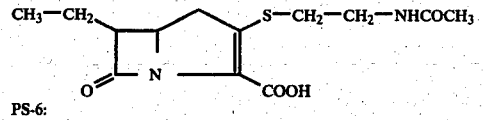

The antibiotic activities shown in Tables I-1 to I-8 above were determined in the following manner.

The minimum inhibitory concentrations of the compounds of formula (I-a-1) or (I-b-1) in Tables I-1 to I-7 and the known compounds in Table I-8 on the various microorganisms shown in the above tables were measured by an agar dilution assay method using a brain heart infusion agar medium "Difco" (a product of Difco Laboratories Inc.)

A sample of the test compound was dissolved in sterile distilled water and diluted to prepare a two-fold dilution series of the compound solution. In a petri plate of 9 cm diameter, 1 ml of the compound solution was added to 9 ml of molten sterile heart infusion agar medium (Difco Laboratories Inc.) at about 60° C. to prepare the compound-containing agar plate. An overnight culture of each test organism indicated in the above table which was prepared by stationary cultivation in Trypto-Soy broth (Eiken Chemi. Co., Ltd.) at 35° C. for 18 to 20 hours, was diluted with the Trypto-Soy broth to give approximately $10^8$ cells/ml and the diluted inoculum was inoculated onto the compound-containing agar plates. After cultivating the plates at 35° C. for 20 hours, the growth of the organism was observed. The minimum concentration of the compound at which no growth of the microorganism was noted was determined, and defined as the minimum inhibitory concentration of the test compound.

The compounds of formula (I-d) of this invention have the following characteristics judging from the antimicrobial spectrum of the compounds of formula (I-b-1) determined in the above manner.

The sodium salts of the antibiotics PS-3, PS-5 and PS-6 which are starting materials for the compounds of formula (I-d) have better antibiotic activity than cephazolin (CEZ) which is most commonly used among known β-lactam type drugs, and is known to be effective against *Pseudomonas aeruginosa* and microorganisms of the genus Serratia, Proteus, Klebsiella, and Enterobacter. The compounds of formula (I-d) generally have better antibiotic activity than the antibiotics PS-3, PS-5 and PS-6 (sodium salts) and in some instances have far superior antibiotic activity. In particular, compounds of formula (I-d) in which $R_2$ represents the aromatic heterocyclic group described hereinabove have about 10 to 20 times as high an antibiotic activity on Gram-positive bacteria as the antibiotics PS-3, PS-5 and PS-6 (sodium salts), and the same or higher activity against Gram-negative bacteria as compared to the known antibiotics (e.g., about 2 to 5 times as high). Compounds of formula (I-d) in which $R_2$ represents a 4-pyridyl group show the best antibiotic activity.

Typical species of the compounds of formula (I-d) were each administered subcutaneously to five mice in a dose of 2 mg. After 5 minutes from the administration, a small amount of blood was periodically drawn from the eyes of the mice into a heparinized capillary tube, and centrifuged. The concentration of the compound in the supernatant liquid (plasma) was determined by a bioassay method using *Comamonas terrigena* B-996. The results as an average on the five mice are given in Table II.

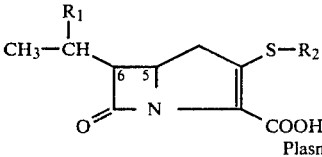

TABLE II

Test for concentration in blood

| A compound of formula (I-d) | | | Dose (mg/mouse) | Plasma of mouse Maximum concentration (μg/ml) | Half period (min.) **** |
|---|---|---|---|---|---|
| $R_1$ | $R_2$ | $R_3$ | | | |
| H | 4-pyridyl | H | 2 | 70.7 | 16.0 |
| —CH$_3$ | 4-pyridyl | H | 2 | 30.7 | 15.2 |
| —OH | 4-pyridyl | H* | 2 | 103.4 | 18.0 |
| —OH | 4-pyridyl | H** | 2 | 29.0 | 13.5 |
| H | pyrimidyl | H | 2 | 48.4 | 29.0 |
| H | pyrimidyl | H | 2 | 23.6 | 22.0 |
| —CH$_3$ | pyrimidyl | H | 2 | 21.2 | 18.2 |
| —OH | pyrimidyl | H* | 2 | 54.0 | 25.0 |
| —OH | pyrimidyl | H** | 2 | 23.3 | 19.0 |
| H | cyclohexyl | Na | 2 | 8.24 | 7.2 |
| H | phenyl | Na | 2 | 11.3 | 25.2 |
| H | —CH$_2$CH$_2$OH | Na | 2 | 36.9 | 6.0 |
| Known compounds | PS-5 . Na*** | | 2 | 40.0 | 7.0 |
| | PS-6 . Na*** | | 2 | 23.8 | 5.0 |
| | PS-3A . Na*** | | 2 | 52.0 | 12.0 |
| | PS-3B . Na*** | | 2 | 26.3 | 5.0 |

*5,6-trans isomer
**5,6-cis isomer
***Sodium salt
****The period that elapsed until the concentration was reduced to half.

The compounds of formula (I-d) tested were well absorbed, and gave considerably high maximum concentrations. In particular, compounds of formula (I-d) in which $R_2$ is the aromatic heterocyclic group gave a superior maximum concentration. Compounds of formula (I-d) in which the S side-chain at the 3-position has a phenyl group (i.e., $R_2$=phenyl) gave a long half period and thus maintained a high blood level over a long period of time.

The in vivo activities of the compounds of formula (I-d) were determined by using mice (five per group, ddy male mice, Shizuoka) which had been intraperitoneally infected with *Staphylococcus aureus* Smith strain in an amount of $5 \times 10^5$ cells per mouse. Two hours after the infection, an injection containing a sodium salt of each of the compounds of formula (I-d) was subcutaneously administered to the mice. The results of the injection treating test ($CD_{50}$) are shown in Table III.

TABLE III

Infection treating test

A compound of above formula (with $R_1$, $R_2$, Z substituents on the bicyclic β-lactam core; $CH_3-CH(R_1)-$ at position 6, $S-R_2$ at position 3, $COOZ$ at position 2)

| $R_1$ | $R_2$ | Z | $CD_{50}$ mg/kg |
|---|---|---|---|
| H | 4-pyridyl | H | 0.063 |
| —CH₃ | 4-pyridyl | H | 0.5 |
| —OH | 4-pyridyl | H* | 0.125 |
| —OH | 4-pyridyl | H** | 0.125 |
| H | 2-pyridyl | H | 0.125 |
| H | 2-pyrimidinyl | H | 0.25 |
| —CH₃ | 2-pyrimidinyl | H | 1.0 |
| —OH | 2-pyrimidinyl | H* | 0.25 |
| —OH | 2-pyrimidinyl | H** | 0.25 |
| H | —CH₂CH₂OH | Na | 1.0 |
| Known comp. PS-5 . Na | | | 1.0 |
| Known comp. PS-6 . Na | | | 8.0 |
| Known comp. PS-3A . Na | | | 4.0 |
| Known comp. PS-3B . Na | | | 2.0 |

*5,6-trans isomer
**5,6-cis isomer

As is clearly seen from the results shown in Table III, the 4-pyridylthio compound, 2-pyridylthio compound and 2-pyrimidinylthio compound showed a better treating effect than the sodium salts of the antibiotics PS-3, PS-5 and PS-6 used as starting materials.

The 4-pyridylthio compound, 2-pyridylthio compound, 2-pyrimidinylthio compound and 3-phenylthio compound which fall into the group of the compounds of formula (I-d) were each administered intraperitoneally to mice in a dose of 20 mg (1 g/kg), but none of them caused the mice to die.

From the data of the in vitro and in vivo activities shown above, it can be concluded that the compounds of formula (I-b-1) and salts thereof are suitable as antimicrobial agents.

The compounds of formula (I), especially (I-d), and the salts thereof have high antimicrobial activities and/or stability both in vitro and in vivo, and can be effectively used as an active ingredient of antimicrobial agents for the prevention, treatment and/or medication of infections and diseases caused by Gram-positive and Gram-negative bacteria not only in humans but also in other animals such as mammals, poultry, and fish.

The compound of formula (I-d) or its salt and compositions containing it may be administered orally, topically or parenterally (e.g., intravenously, intramuscularly, intraperitoneally) in a variety of usual pharmaceutical preparations depending on the method of administration. For example, the compound of formula (I-d) or its salt may be formulated with a pharmaceutically acceptable carrier, diluent or the like into solids (e.g., tablets, capsules, powders, granules, sugar-coated tablets, troches, powder sprays, suppositories), semi-solids (e.g., ointments, creams, semisolid capsules), or liquids (e.g., solutions, emulsions, suspensions, lotions, syrups, injecting solutions, liquid sprays).

A unit dose preparation comprising the compound of formula (I-d) or its salt may generally contain from 0.1 to 99% by weight of the active component in any of liquid, semisolid and solid forms. The content of the active ingredient in the pharmaceutical preparation may vary depending upon the type of the formulation or its amount. Usually, it may be from about 10 mg to about 1000 mg, preferably from about 100 mg to about 1000 mg.

Typical carriers, fillers, diluents or the like which can be used in these preparations and methods of making these preparations are described below.

Tablets and capsules for oral administration may be in a unit dose form and may contain binding agents such as syrup, acacia, gelatin, sorbitol, tragacanth, polyvinylpyrrolidone or the like; fillers such as lactose, sucrose, starch, calcium phosphate, sorbitol, glycine or the like; lubricants such as magnesium stearate, talc, polyethylene glycol, silica or the like; disintegrants such as potato starch or the like; or wetting agents such as sodium lauryl sulfate or the like. The tablets may be coated according to methods well known in the art.

Liquid preparations for oral uses may be in the form of oily or aqueous suspensions, solutions, emulsions, syrups, etc., or may be provided as dry products that can be combined with water or other suitable vehicles before use. The said liquid preparations for oral uses may contain pharmaceutically acceptable ingredients, for example, suspending agents (for example, methyl cellulose, sorbitol syrup, sugar syrup, hydroxyethyl cellulose, gelatin, carboxymethyl cellulose, aluminum stearate gel, hydrogenated edible fats and oils); emulsifying agents (for example, acacian lecithin, sorbitan monooleate); non-aqueous vehicles (for example, ethyl alcohol, propylene glycol, oily esters, fractionated coconut oil, almond oil); and preservatives (for example, methyl p-hydroxybenzoate, propyl p-hydroxybenzoate, sorbic acid).

Suppositories may contain conventional suppository bases like cocoa butter and various glycerides.

Compositions for injection may be prepared in unit dose form in ampoules or in multidose containers with a preservative. They may be in the form of suspensions, solutions and emulsions in oily or aqueous vehicles, and if necessary, may contain formulatory agents such as suspending agents, dispersing agents and stabilizing agents. Alternatively, the antibiotic of the present invention may be prepared in powder form which can be combined with pyrogen-free, sterile water before use.

Compositions containing the compound of formula (I-d) and/or it salt may be provided in various forms suitable for absorption through the mucous membrane of the nose, throat and bronchial tube. For example, the form of powder or liquid sprays, inhalants, troches, throat paints, etc. is advantageous for these purposes. For treatment of the ears and eyes, the antibiotic of the present invention may be formulated as individual capsules, as drops, in liquid or semi-solid form, etc. For topical applications it may be prepared as formulations in hydrophilic or hydrophobic bases such as powders, lotions, creams, ointments, and the like.

If desired, in addition to a carrier, the compositions described above may contain other ingredients, for example, preservatives, antioxidants, lubricants, viscosity agents, flavoring agents, suspending agents, binders, stabilizing agents, and the like.

When the compounds of formula (I-d) and/or their salts are intended for treatment of infections in pigs, cows, sheep, chickens and the like, the formulations may be prepared as intramammary preparations in long-acting or quick-releasing bases, for instance, or as feed additive concentrates. The above described pharmaceutical compositions according to the present invention may contain the compound of formula (I-d) and/or its salt as the sole active ingredient or in combination with other therapeutically effective ingredients.

As described above in detail, because the compounds of formula (I-d) and their salts have a synergistic effect against various $\beta$-lactamase producing bacteria in combination with $\beta$-lactam compounds, it will be advantageous to combine them with $\beta$-lactam compounds in pharmaceutical compositions. Examples of suitable $\beta$-lactam compounds include penicillin derivatives such as benzylpenicillin, phenoxymethylpenicillin, carbenicillin, ampicillin and amoxicillin; and cephalosporin derivatives such as cephaloridine, cephalotin, cephazolin, cephalexin, cefoxitin, cephacetrile, cephamandole, cephapirin, cephradine and cephaloglycin.

When the compound of formula (I-d) and/or its salt is combined with one or more members of the above listed $\beta$-lactam compounds, the combining ratio of the antibiotic of this invention to the known $\beta$-lactam compound is not critical, but may vary in a wide range. From the practical viewpoint, however, it is advisable to use the quantitative ratio of the antibiotic of this inventions to the known $\beta$-lactam compound in the range of 20:1 to 1:150, and preferably 10:1 to 1:100.

In the treatment of bacterial infections in mammals, the dose of the compound of formula (I-d) and/or its salt can be varied depending on the subject to be treated, the body weight, the type, severity and symptoms of infections, the mode and number of administrations, etc. For usual oral or parenteral administration, it is advantageous to use a daily dose in the range of 0.05 mg/kg to 500 mg/kg, preferably 0.5 mg/kg to 200 mg/kg, more preferably in a divided dosage. It is clear that a dose beyond the above recommended range may also be employed depending on the individual conditions of the subject to be treated.

The compound of formula (I-d) and/or its salt can be used in pharmaceutical compositions as described above, and may also be added directly or as feed additive concentrates in animal feeds. In addition, they may be utilized as the active ingredients for food preservatives or disinfectants.

The following Examples illustrate the present invention more specifically.

The following Reference Examples illustrate the fermentative production of sodium salts of a 5,6-trans-isomer and a 5,6-cis-isomer of antibiotic PS-3, i.e. 3-(2-acetamidoethylthio)-6-(1-hydroxyethyl)-7-oxo-1-azabicyclo[3.2.0]hept-2-ene-2-carboxylic acid, which are termed "PS-3A.sodium salt" and "PS-3B.sodium salt", respectively, and the antibiotic substance PS-5, i.e. 3-(2-acetaminothylthio)-6-ethyl-7-oxo-1-azabicyclo-[3.2.0]hept-2-ene-2-carboxylic acid, and the antibiotic PS-6, i.e. 3-(2-acetamidoethylthio)-6-isopropyl-7-oxo-1-azabicyclo[3.2.0]hept-2-ene-2-carboxylic acid, which were used as starting materials in Examples to be given hereinbelow.

REFERENCE EXAMPLE 1

Production of antibiotic substances PS-3A and PS-3B sodium salts:

A platinum loopful of Streptomyces sp. A271 (ATCC 31358) inoculated in a slant having the composition ISP-2 shown hereinbelow was inoculated into 100 ml of a culture medium of the composition SE-4 shown hereinbelow in an Erlenmeyer flask, and cultivated at 28° C. for 2 days to prepare a seed culture. The seed culture was inoculated in each of three 30-liter jar fermentors containing 15 liters of a culture medium having the composition ABG-7' shown hereinbelow. It was cultivated at 28° C. for 96 hours at an air flowing rate of 7.5 liters/minute with stirring at 200 rpm. To the culture broth was added 2 kg of Topco Perlite (a product of Toko Perlite Kogyo K.K.), and the mixture was filtered by a filter press to collect 35 liters of the filtrate (total antibiotic activity $1.26 \times 10^7$ CCU). The subsequent operations were performed at a low temperature of less than 10° C.

The filtrate so obtained was passed through a column ($7.2 \times 80$ cm) packed with 3 liters of Diaion PA306 (a product of Mitsubishi Chemical Industries, Ltd.) to cause adsorption of the active portions. The column was eluted with 20 liters of 5% (W/V) aqueous sodium chloride solution. The eluates were passed through a column packed with 3 liters of Diaion HP-20 (a product of Mitsubishi Chemical Industries, Ltd.) to cause adsorption of active portions, and the column was eluted with 10 liters of 30% (v/v) acetone. 800 ml of the active portions were collected, concentrated, and adsorbed to a column (1.5×30 cm) of QAE-Sephadex (A-25) (Pharmacia Fine Chemicals Co.) equilibrated with a phosphate buffer (M/100; pH 8.4). The column was eluted with 2 liters of an M/100 phosphate buffer (pH 8.4) by linearly increasing the concentration of sodium chloride in it from 0 to 0.4 M. The eluate was fractionated into 17 g fractions. Active fractions Nos. 27 to 46 detected by antibacterial activity against Comamonas terrigena were collected, and after adding sodium chloride to a concentration of 3% (W/V), were adsorbed to a column (1.2×30 cm) of Diaion HP-20AG (200 to 400 mesh). The column was eluted with 400 ml of an aqueous solution of acetone with the concentration of acetone increasing linearly from 0 to 5% (v/v). The eluate was fractionated into 8 g fractions. Active fractions Nos. 22 to 53 detected as above were collected, and lyophilized to afford 560 mg of a pale yellow dry crude powder of antibiotics PS-3A and 3B.

The powder was dissolved in 1 ml of a phosphate buffer (M/100; pH 8.4). The solution was applied to a column (1.1×90 cm) of Sephadex G-10 (a product of Pharmacia Fine Chemicals Co.) and developed with the same buffer. Active fractions were collected after measuring their ultraviolet absorption (λ 300 nm). These active fractions were adsorbed onto a column (1.1×20 cm) of QAE Sephadex A-25 equilibrated with a phosphate buffer (M/100; pH 8.4) and eluted with 200 ml of a phosphate buffer (m/100; pH 8.4) with the concentration of sodium chloride increasing linearly from 0 to 0.15 M. Active fractions were collected, and sodium chloride was added to a centration of 3% (w/v). The active fractions were then adsorbed to a column (1.1×20 cm) of Diaion HP-20AG (200 to 400 mesh), and eluted with water. The absorption intensities of the fractions at 300 nm were measured, and the fractions were separated into two portions by peaks. These portions were each lyophilized to afford 43 mg of antibiotic PS-3B, and then 40 mg of antibiotic PS-3A.

| Composition of a slant medium (ISP-2) | |
|---|---|
| Glucose | 0.4% (w/v) |
| Malt extract | 1.0 (w/v) |
| Yeast extract | 0.4 (w/v) |
| Agar | 1.5 (w/v) |
| pH: 7.0 before sterilization | |
| Composition of seed culture (SE-4) | |
| Beef extract (Difco Laboratories) | 0.3% (w/v) |
| Bacto-tryptone (Difco Laboratories) | 0.5 (w/v) |
| Glucose | 0.1 (w/v) |
| Soluble starch | 2.4 (w/v) |
| Yeast extract | 0.5 (w/v) |
| Calcium carbonate | 0.4 (w/v) |
| Defatted soybean meal | 0.5 (w/v) |
| pH: 7.5 before sterilization | |
| Composition of a production medium (AGB-7') | |
| Maltose | 3% (w/v) |
| Dry yeast | 2 (w/v) |
| Sodium chloride | 0.5 (w/v) |
| Dipotassium phosphate | 0.05 (w/v) |
| Magnesium chloride | 0.05 (w/v) |
| Calcium carbonate | 0.3 (w/v) |
| Defatted soybean meal | 0.3 (w/v) |
| Peptone (Kyokuto Co.) | 0.05 (w/v) |
| Cobalt chloride | 0.00013 (w/v) |

[I] Physico-chemical properties and biological properties of antibiotic PS-3A:

(1) Color
Colorless (2) Solubility
Readily soluble in water, and substantially insoluble in acetone.

(3) Paper chromatography
The antibiotic PS-3A (sodium salt) shows the following Rf values when developed with the following solvents using Toyo Filter Paper No. 50 (a product of Toyo Roshi Kaisha Ltd.) by a descending method.

| Acetonitrile/tris/EDTA (*1): | Rf = 0.19 |
|---|---|
| Ethanol/water (7/3): | Rf = 0.59 |

(*1): A mixed solvent consisting of 120 ml of acetonitrile, 30 ml of a 1/10M tris(hydroxymethyl)-aminomethane/HCl buffer (pH 7.5), and 1 ml of a 1/10M aqueous solution of sodium ethylenediaminetetraacetate).

(4) Thin-layer chromatography (TLC)
The antibiotic PS-3A (sodium salt) shows the following Rf values when developed with the following solvents by thin-layer chromatography using Chromagram Sheet 13254 Cellulose (No. 6065) (a trademark for a product of Eastman Kodak Co.).

| n-Butanol/ethanol/water (4/1/5): (upper layer) | Rf = 0.30 |
|---|---|
| n-Butanol/isopropanol/water (7/7/6): | Rf = 0.42 |
| Acetonitrile/water (8/2): | Rf = 0.29 |

(5) High voltage paper electrophoresis
The antibiotic PS-3A (sodium salt) shows the following behavior in a buffer solution having the following composition when it is subjected to electrophoresis on Toyo Filter Paper No. 50 (Toyo Roshi Kaisha Ltd.) by using a high voltage paper electrophoresis apparatus (Savant Instrument Inc., High Voltage Power Supply HV 3000 A, Electrophoresis Chamber FP 18A).

The antibiotic is seen to migrate through a distance of at least 5 mm, usually 10 to 40 mm, toward the anode when an electric current is passed for 30 minutes on a potential gradient of 42 V/cm in a buffer (pH 8.6) composed of 3000 ml of water, 3.3 g of barbital and 25.5 g of sodium barbital.

(6) Ultraviolet absorption spectrum
The ultraviolet absorption of a solution of 90 micrograms of the antibiotic PS-3 sodium salt in 3 ml of water (pH 7.0) is measured by using a double beam spectrophotometer (Hitachi Model 200-20). The characteristic UV absorption values are as follows:

$\lambda_{min}^{H2O}$ = about 242.5 nm.
$\lambda_{max}^{H2O}$ = about 300.0 nm.

An aqueous solution of hydroxylamine having a pH of 7.5 is added to a solution of the above substance in deionized water so that the concentration of the antibiotic PS-3 to about 20 μg/ml and the concentration of hydroxylamine to 10 mM. When the mixed solution is allowed to stand at 22° C. for 30 minutes, about 93% of its absorbance at 300.0 nm disappears.

(7) Infrared absorption spectrum
Characteristic absorption maxima of the antibiotic PS-3 measured by a KBr method by means of an infrared spectrophotometer (Hitachi Model 260-30) are as follows:
(1) About 1770 cm$^{-1}$ (—CO— of the β-lactam ring)
(2) about 1640 cm$^{-1}$ (—CO— of amide)
(3) about 1590 cm$^{-1}$ (—COO$^{\ominus}$)
(4) about 1550 cm$^{-1}$ (—CO—NH— of amide)
(8) Proton NMR spectrum The antibiotic PS-3A shows the following characteristic signals in a 100 MHz proton NMR spectrum (internal reference: d$_4$-sodium 3-trimethylsilylpropionate) measured in heavy water (D$_2$O) by using Nippon Denshi JNM PS-100.

(1) A doublet centered at about 1.37 ppm $$(J = \text{about 6.5Hz; } CH_3—\underset{|}{CH}—)$$

(2) A sharp singlet at about 2.04 ppm ($\underline{CH_3}$—CO—)
(3) A multiplet at about 2.75–3.55 ppm $$(-CH_2-, -CHOH-\underset{|}{CH}-, -S-CH_2-CH_2-NH-)$$

(4) A multiplet at about 4.01–4.32 ppm $$(-\underset{\underset{N}{|}}{CH}-, CH_3-\underline{CH}OH)$$

(5) A multiplet at 4.68–4.90 ppm
(9) Color reactions
Ehrlich reagent reaction: positive
Iodine-chloroplatinic acid reaction: positive
Ninhydrin reaction: negative

[II] Physico-chemical properties and biological properties of antibiotic PS-3B:

(1) Ultraviolet absorption spectrum
Measured in the same way as in the case of the antibiotic PS-3A. The characteristic values are as follows:
$\lambda_{min}^{H2O}$ = about 242.5 nm
$\lambda_{max}^{H2O}$ = about 298.0 nm (2) Proton NMR spectrum
Measured in the same way as in the case of the antibiotic PS-3A. The characteristic signals are as follows:
(1) A doublet centered at about 1.38 ppm $$(J = \text{about 6.5Hz, } CH_3—\underset{|}{CH}—)$$

(2) A singlet at about 2.04 ppm ($\underline{CH_3}$—CO—)
(3) A multiplet at about 2.80–3.80 ppm $$(-CH_2-, -S-CH_2-CH_2-NH, -\underset{|}{C}HOH-\underset{|}{CH}-)$$

(4) A multiplet at about 4.01–4.50 ppm $$(-\underset{\underset{N}{|}}{CH}-, CH_3-\underline{CH}OH)$$

(5) A multiplet at about 4.65–4.90 ppm (3) Other properties
The behaviors of the PS-3B is paper chromatography, thin-layer chromatography and high voltage paper electrophoresis are quite identical to those of the antibiotic PS-3A. The characteristic absorption maxima in an infrared absorption spectrum of PS-3B are almost the same as those of the antibiotic PS-3A.

REFERENCE EXAMPLE 2

Production of PS-5 sodium salt and PS-6 sodium salt:
A seed culture in a flask of Streptomyces sp. A271 (ATCC 31358) was prepared. One hundred milliliters of the seed culture was inoculated in two 3-liter jar fermentors containing 15 liters of the SE-4 medium, and cultivated at 28° C. for 24 hours with stirring at 200 rpm at an air flow rate of 7.5 liters/minute. Thirty liters of the resulting culture broth was inoculated in a 1-kiloliter stainless steel fermentation tank containing 700 liters of an AGB-42 medium (described hereinbelow), and cultivated at 28° C. for 72 hours with stirring at 170 rpm at a flow rate of 300 liters/minute. The supernatant liquid resulting from centrifugation of the culture broth had an antibiotic potency of 1040 CCU/ml.

To the culture borth was added 3% (W/V) of Topco Perlite as a filtration aid (a product of Toko Perlite Kogyo K.K.) and it was filtered by a filter press, and washed with water to obtain 600 liters of a filtrate (total antibiotic activity $5.09 \times 10^8$ CCU).

The operations subsequent to this were performed at 6° C.

The filtrate was first passed through a column packed with 10 liters of an ion exchange resin (Diaion PA-306, a product of Mitsubishi Chemical Industries, Ltd.) to decolorize it (the total antibiotic activity in the effluent was $3.70 \times 10^8$ CCU; yield 73%).

The effluent was adsorbed to a column packed with 20 liters of Diaion HP-20 (a product of Mitsubishi Chemical Industries, Ltd.), and eluted by a gradient method with 60 liters in total of an aqueous solution of acetone with the concentration of acetone increasing linearly from 0 to 80%. The eluate was fractionated into 2-liter fractions. Each of the fractions was analyzed by descending paper chromatography [developed with a mixed solvent consisting of 20 ml of acetonitrile, 30 ml of a 1/10 M tris(hydroxymethyl)aminomethane-HCl buffer having a pH of 7.5 and a 1/10 M aqueous solution of sodium ethylenediaminetetraacetate having a pH of 7.5) and bioautography, and two active portions, one consisting of fractions Nos. 4 to 8 and the other consisting of fractions Nos. 9 and 10, were collected. The first portion mainly contained antibiotic PS-5 (the total antibiotic activity $2.54 \times 10^8$ CCU; yield 49%), and the second portion was a mixture of the antibiotic PS-6 and antibiotic PS-5 (the total antibiotic activity $3.13 \times 10^7$ CCU; yield 6.1%). The content of the antibiotic PS-6 in the mixture was about one-tenth of the total antibiotic activity. The PS-5 sodium salt was separated and purified from the first portion, and PS-6 was separated and purified from the second portion, in the following manner.

(1) Purification of PS-5 sodium salt
The first portion was adsorbed to a column packed with 5 liters of Diaion PA306S (a product of Mitsubishi Chemical Industries, Ltd.) and washed with 2 liters of water. The column was eluted by a gradient method with 20 liters in total of an aqueous solution of sodium chloride with the concentration of sodium chloride increasing linearly from 0 to 3%. The elute was fractionated into 500 ml fractions. Active fractions Nos. 23 to 45 were collected to obtain 10.5 liters of an active eluate ($1.98 \times 10^8$ CCU; yield 39%). The active eluate was adsorbed to a column packed with 4 liters of Diaion HP-20, and eluted by a gradient method with 10 liters in total of an aqueous solution of acetone with the concentration of acetone increasing linearly from 0 to 25%. The eluate was fractionated into 100 ml fractions. Active fractions Nos. 59 to 73 were collected to obtain 1.5 liters of an active eluate ($1.58 \times 10^8$ CCU; yield 31%). The active eluate was treated under reduced pressure to remove acetone, and adsorbed to a column (3.4 cm in diameter and 60 cm in length) packed with 500 ml of QAE-Sephadex (a product of Pharmacia Fine Chemicals Co.). The column was eluted by a gradient method with 5 liters of an aqueous solution of sodium chloride with the concentration of sodium chloride increasing linearly from 0 to 2%, and the eluate was fractionated into 20 ml fractions. Active fractions Nos. 88 to 133 were collected to obtain 900 ml of an active eluate ($1.31 \times 10^8$ CCU; yield 26%).

The pH of the active eluate was carefully adjusted to 8.3 with 1% NaOH, and then it was adsorbed to a column (3.4 cm in diameter and 65 cm in length) packed with 600 ml of Diaion HP-20AG (a product of Mitsubishi Chemical Industries, Ltd.). The column was eluted by a gradient method with 3 liters of an aqueous solution of acetone with the concentration of acetone increasing linearly from 0 to 10%, and the eluate was fractionated into 20 ml fractions. Active fractions Nos. 56 to 71 were collected to obtain 320 ml of an active eluate ($1.19 \times 10^8$ CCU; yield 23%). The active eluate was lyophilized to afford 12.4 g of a yellow powder (8400 CCU/mg).

The yellow powder was dissolved in 50 ml of a 0.01 M sodium phosphate buffer (pH 8.0), and applied to a column (5.6 cm in diameter and 90 cm in length) packed with 2 liters of Sephadex G-10 (Pharmacia Fine Chemicals Co.). The column was eluted with a 0.01 M sodium phosphate buffer (pH 8.0), and the eluate was fractionated into 10 ml fractions. Active fractions Nos. 85 to 121 were collected to obtain 360 ml of an active eluate ($9.3 \times 10^7$ CCU; yield 18%). The active eluate was adsorbed to a column (3.0 cm $\times$ 43 cm) packed with 300 ml of QAE-Sephadex A-25 (Pharmacia Fine Chemicals Co.), and the column was eluted by a gradient method with 2 liters in total of an aqueous solution of sodium chloride with the concentration of sodium chloride increasing linearly from 0 to 1.5%. The eluate was fractionated into 20 ml fractions. Active fractions Nos. 42 to 63 were collected to obtain 440 ml of an active eluate ($8.8 \times 10^7$ CCU; yield 17%).

The pH of the active eluate was carefully adjusted to 8.3 with 1% NaOH, and it was adsorbed to a column (3.0 cm in diameter and 44 cm in length) packed with 300 ml of Diaion HP-20AG (a product of Mitsubishi Chemical Industries, Ltd.). The column was eluted by a gradient method with 2 liters in total of an aqueous solution of acetone with the concentration of acetone increasing linearly from 0 to 10%, and the eluate was fractionated into 10 ml fractions. Active fractions Nos. 54 to 86 were collected, and lyophilized to afford 3.38 g of colorless powder (25,000 CCU/mg).

(2) Purification of PS-6 sodium salt

The second portion was adsorbed to a column ($3.4 \times 60$ cm) packed with Diaion PA-306 (a product of Mitsubishi Chemical Industries, Ltd.), and eluted by a gradient method with 3 liters in total of an aqueous solution of a sodium chloride with the concentration of sodium chloride increasing linearly from 0 to 4.5%. The eluate was fractionated into 50 g fractions. These fractions were analyzed by bioassay, and active fractions were collected (total antibiotic activity $2.62 \times 10^7$ CCU; yield 5.1%). The active fractions were adsorbed to a column (2.0 cm in diameter and 25 cm in length) packed with Diaion HP-20, and eluted with a 10% aqueous solution of acetone. The eluate was fractionated into 30 ml fractions. Active fractions Nos. 8 to 15 were collected to obtain 240 ml of an active eluate ($1.83 \times 10^7$ CCU; yield 3.6%). The active eluate was concentrated under reduced pressure to remove actone. The residue was adsorbed to a column (2.4 cm in diameter and 30 cm in length) of QAE-Sephadex (a product of Pharmacia Fine Chemicals Co.) which had been equilibrated with a M/100 phosphate buffer (pH 8.0). The column was eluted by a gradient method with a M/100 phosphate buffer by linearly increasing its sodium chloride concentration from 0 to 0.4 M, and the eluate was fractionated into 10 g fractions. Each of the fractions was diluted to 100 times, and analyzed by ultraviolet absorption spectroscopy and bioassay. Thus, active fractions Nos. 25 to 43 were collected to obtain 190 ml of an active eluate ($1.58 \times 10^6$ CCU; yield 3.1%.

To remove the antibiotic PS-5 completely, the active eluate was adsorbed to a column (1.2 cm in diameter and 40 cm in length) packed with Diaion HP-20AG (a product of Mitsubishi Chemical Industries, Ltd.), and eluted by a gradient method with 300 ml in total of an aqueous solution of methanol with the concentration of methanol increasing linearly from 10 to 75%. The eluate was fractionated into 4 g fractions. Each of the fractions was analyzed by descending paper chromatography and bioautography, and two active portions, one consisting of fractions Nos. 26 to 33 containing the antibiotic PS-5 and the other consisting of fractions Nos. 35 to 45 containing the antibiotic PS-6, were collected. The second portion containing the antibiotic PS-6 ($5.8 \times 10^6$ CCU; yield 1.1%) was concentrated to remove methanol, and then lyophilized. To purify the resulting powder further, it was dissolved in 1 ml of a M/100 phosphate buffer (pH 8.0). The solution was applied to a column (5.6 cm in diameter and 80 cm in length) packed with Sephadex G-10 (a product of Pharmacia Fine Chemicals Co.), and eluted with the same phosphate buffer. The eluate was fractionated into 10 g fractions. Active fractions Nos. 85 to 92 were collected to obtain 80 ml of an active eluate ($5.08 \times 10^5$ CCU; yield 1.1%). The active eluate was adjusted to pH 8.3 with an aqueous sodium hydroxide solution, and adsorbed to a column (2.0 cm in diameter and 30 cm in length) packed with Diaion HP-20 (Mitsubishi Chemical Industries, Ltd.). The column was eluted with a 10% aqueous solution of acetone. The eluate was lyophilized to obtain 205 mg of a white powder.

| Formulation of a production medium (AGB-42) | |
|---|---|
| Maltose | 5.0% (W/V) |
| Soluble starch | 1.0 (W/V) |
| Glycerin | 0.3 (W/V) |
| Dry yeast | 3.0 (W/V) |
| Sodium chloride | 0.5 (W/V) |
| Dipotassium phosphate | 0.05 (W/V) |
| Magnesium sulfate (MgSO$_4$ . 7H$_2$O) | 0.05 (W/V) |
| Calcium carbonate (CaCO$_3$) | 0.3 (W/V) |
| Cobalt chloride | 0.00013 (W/V) |

| Formulation of a production medium (AGB-42) |
|---|
| (CoCl$_2$ . 6H$_2$O) |
| pH: 7.0 before sterilization |

EXAMPLE 1

Production of p-nitrobenzyl 3-(2-acetamidoethylthio)-6-ethyl-7-oxo-1-azabicyclo[3.2.0]hept-2-ene-2 carboxylate (PS-5.p-nitrobenzyl ester)

PS-5 sodium salt (275 mg) was dissolved in 20 ml of dry dimethylformamide, and with stirring at room temperature, 197 microliters of triethylamine was added. Ten minutes later, a solution of 179 mg of p-nitrobenzyl bromide in 5 ml of dry dimethylformamide was added at 5° C. with stirring, and the mixture was stirred at room temperature for 3 hours. After the reaction, the reaction mixture was poured into 150 ml of benzene, and washed three times with 100 ml of a phosphate buffer (0.1 M; pH 6.8). The product was dried over anhydrous sodium sulfate, and the solvent was distilled off under reduced pressure. The residue was chromatographed on a column of silica gel (30 g, 1.8×30 cm) using a benzene-acetone (3:1) as an eluent. The eluates were distilled to remove the solvent and thereby to obtain yellow crystals. Recrystallization of the yellow crystals from benzene afforded 240 mg of yellow needles having a melting point of 163° to 165° C.

$[\alpha]_D^{21}$ +70.7° (c 1.00, CHCl$_3$).
UV$\lambda_{max}^{CHCl_3}$ nm($\epsilon$): 322 (12800), 269 (12000).
IR$\nu_{max}^{CHCl_3}$ cm$^{-1}$: 3460 (NHCO), 1780 (CO of β-lactam), 1710 (CO of ester), 1675 (NHC0), 1530 (NO$_2$), 1350 (NO$_2$).
NMR (CDCl$_3$)δ: 1.04 (3H, t, J=7 Hz, CH$_2$CH$_3$), 1.84 (2H, m, CH$_2$CH$_3$), 1.96 (3H, s, NHCOCH$_3$), 2.80–3.60 (7H, m, 3XCH$_2$, CH), 3.98 (1H, dt, J=9.0 Hz, J=3 Hz, C-5H), 5.19 (1H, d, J=14 Hz, ArCH.H), 5.49 (1H, d, J=14 Hz, ArCH.H), 5.95 (1H, brs, NH), 7.61 (2H, d, J=9 Hz, ArH), 8.18 (2H, d, J=9 Hz, ArH).
Mass (m/e): 433 (M+), 363 (M+—EtCH=C=O).
Anal. Calcd. for C$_{20}$H$_{23}$O$_6$N$_3$S: C: 55.43: H, 5.35: N, 9.70. Found: C, 55.29: H, 5.24: N, 9.40.

The compounds shown in the following Examples 2 to 6 were obtained by the same method as in Example 1.

EXAMPLE 2

PS-5-.benzyl ester $[\alpha]_D^{21}$ +19.97° (c 0.33, CHCl$_3$).
UV$\lambda_{max}^{MeOH}$ nm($\epsilon$): 318 (11000).
IR$\lambda_{max}^{CHCl_3}$ cm$^{-1}$: 3430 (CONH), 1770 (CO of β-lactam), 1690 (CO of ester), 1665 (CONH).
NMR (CDCl$_3$)δ: 1.04 (3H, t, J=7 Hz, CH$_2$CH$_3$), 1.82 (2H, m, CH$_2$CH$_3$), 1.96 (3H, s, COCH$_3$), 2.80–3.60 (7H, m, 3XCH$_2$, CH) 3.94 (1H, dt, J=9.0 Hz, J=3 Hz, C-5, H), 5.21 (1H, d, J=12 Hz, ArCH.H), 5.38 (1H, d, J=12 Hz, ArCH.H), 5.90–6.10 (1H, brs, NH), 7.34 (5H, distorted, s, ArH).
Mass (m/e): 388 (M+).

EXAMPLE 3

PS-5.benzhydryl ester $[\alpha]_D^{21}$ +2.55° (C=0.33, CHCl$_3$).
UV$\lambda_{max}^{MeOH}$ nm($\epsilon$): 320 (11200).
IR$\lambda_{max}^{CHCl_3}$ cm$^{-1}$: 3450 (—CONH—), 1775 (CO of β-lactam), 1675 (CO of ester).
NMR (CDCl$_3$)δ: 1.06 (3H, t, J=8 Hz, CH$_3$CH$_2$—), 1.94 (3H, s, CH$_3$CONH—), 3.94 (1H, dt, J=9 Hz, J=3 Hz, C-5H), 5.92 (1H, brs, NH), 6.90 (1H, s, —CHAr$_2$), 7.32 (10H, s, —CHAr$_2$).
Mass (m/e): 464 (M+), 394 (M+—EtCH=C=O).

EXAMPLE 4

PS 5.methyl ester $[\alpha]_D^{21}$ +72.23° (C=0.36, CHCl$_3$).
UV$\lambda_{max}^{MeOH}$ nM($\epsilon$): 315 (10300).
IR$\lambda_{max}^{CHCl_3}$ cm$^{-1}$: 3450 (—CONH—), 1775 (CO of β-lactam), 1675 (CO of ester).
NMR (CDCl$_3$) δ: 1.06 (3H, t, J=8 Hz, —CH—CH$_3$), 1.70–2.06 (2H, m, —CH$_2$—CH$_3$), 1.99 (3H, s, —NH-COCH$_3$), 2.90–3.56 (7H, m, 3X—CH$_2$—, —CH—), 3.83 (3H, s, —CO$_2$CH$_3$), 3.96 (1H, dt, J=8 Hz, J=2 Hz, C-5H), 6.20 (1H, brs, -NH).
Mass (m/e): 312 (M+), 242 (M+—EtCH=C=O).

EXAMPLE 5 p-Nitrobenzyl 3-(2-acetamidoethylthio)-6-iospropyl-7-oxo-1-azabicyclo[3.2.0]hept-2-ene-2-carboxylate (PS-6. p-nitrobenzyl ester)

UV$\lambda_{max}^{THF}$ nm($\epsilon$): 322 ($\epsilon$=12500), 269 (11800)
IR$\lambda_{max}^{CHCl_3}$ cm$^{-1}$: 1780 (CO of β-lactam), 1708 (CO of ester).
NMR (CDCl$_3$)δ:

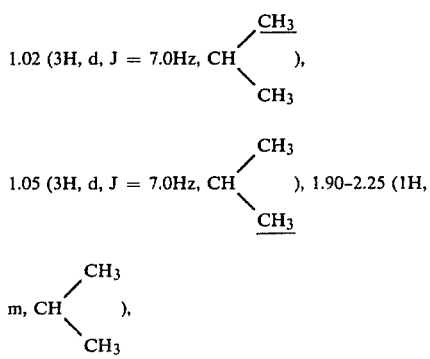

1.98 (3H, S, COCH$_3$), 2.80–3.60 (7H, m, C-4H, C-6H, 2×CH$_2$), 4.02 (1H, dt, J=9.0 Hz, J=3.0 Hz, C-5H), 5.20 (1H, d, J=14.0 Hz, ArCHH), 5.48 (1H, d, J=14.0 Hz, ArCHH), 6.00 (1H, m, NH), 7.62 (2H, d, J=9.0 Hz, ArH), 8.18 (2H, d, J=9.0 Hz, ArH).

EXAMPLE 6

PS-6.benzyl ester

UV$\lambda_{max}^{MeOH}$ 318 nm.
IR$\lambda_{max}^{CHCl_3}$ cm$^{-1}$: 3400 (NH-CO), 1765 (CO of β-lactam), 1665 (NHCO).
NMR (CDCl$_3$) δ: 1.07 (6H, t, J=8 Hz, —CH.(CH$_3$)$_2$), 2.00 (3H, s, —NHCOCH$_3$), 4.05 (1H, dt, J=9.0 Hz, J=3.0 Hz, C-5H), 5.31 (1H, d, J=12 Hz, -CHHAr), 5.47 (1H, d, J=12 Hz, —CHHAr), 6.07 (1H, brs, —NH—), 7.46 (5H, s, Ar-H).
Mass (m/e): 402 (M+), 318 (M+-i.Pr.CH=C=O).

EXAMPLE 7

Production of p-nitrobenzyl 5,6-trans-3-(2-acetamidoethylthio)-6-(1-hydroxyethyl)-7-oxo-1-azabicyclo[3.2.0]hept-2-ene-2-carboxylate (PS-3A.p-nitrobenzyl ester.

Triethylamine (245 microliters) was added to a solution of 88 mg of PS-3A sodium salt (purity 64%) in 10 ml of dry dimethylformamide, and while the mixture was stirred under ice cooling in a stream of nitrogen, a solution of 346 mg of p-nitrobenzyl bromide in 1 ml of dry dimethylformamide was added. After stirring the mixture at room temperature for 3 hours, the reaction mixture was poured into 30 ml of ethyl acetate, and washed three times with 15 ml of a phosphate buffer (0.1 M; pH 6.8). The solvent layer was dried over anhydrous sodium sulfate, and distilled off under reduced pressure at less than 30° C. The residue was washed three times with 5 ml of methylene chloride to afford 54.0 mg of a white powder of the captioned compound. The methylene chloride layer was concentrated to 5 ml, then adsorbed to a silica gel column (4 g, 1.0×10.5 cm, Kiesel gel 60, 70–230 mesh, a product of E. Merck Co.), and then developed with benzene-acetone (1:1) to obtain fractions containing the captioned compound. Evaporation of the solvent under reduced pressure also afforded 12.2 mg of the white powder.

UV$\lambda_{max}^{THF}$ nm($\epsilon$): 322 (13500), 270 (11500).

IR$\lambda_{max}^{KBr}$ cm$^{-1}$: 3475, 3300 (OH, NH), 1765 (CO of $\beta$-lactam), 1700 (CO of ester), 1650 (CO of amide).

NMR (CDCl$_3$)$\delta$: 1.37 (3H, d, J=6.5 Hz, —CHOH-C$\underline{H}_3$), 1.96 (3H, S, —COC$\underline{H}_3$), 2.50–3.65 (7H, m, C6-$\underline{H}$, C4-H$_2$, —S—CH$_2$—CH$_2$—NH—), 3.80–4.40 (2H, m, —C$\underline{H}$OH—CH$_3$, C5-$\underline{H}$), 5.21 (1H, d, J=14.0 Hz, —C$\underline{H}$H—Ar), 5.45 (1H, d, J=14.0 Hz, —CH$\underline{H}$-Ar),

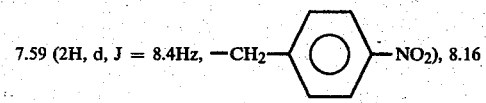

7.59 (2H, d, J = 8.4Hz, —CH$_2$—⟨O⟩—NO$_2$), 8.16

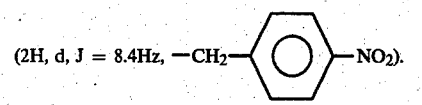

(2H, d, J = 8.4Hz, —CH$_2$—⟨O⟩—NO$_2$).

Mass (m/e): 363 (M+-86).

EXAMPLE 8

Production of p-nitrobenzyl 5,6-cis-3-(2-acetamidoethylthio)-6-(1-hydroxyethyl)-7-oxo-1-azabicyclo[3.2.0]hept-2-ene-2-carboxylate (PS-3B.p-nitrobenzyl ester)

Example 7 was repeated except that PS-3B was used as a starting material instead of PS-3A.

UV$\lambda_{max}^{THF}$ nm($\epsilon$): 320 (11500), 270 (9700).

IR$\lambda_{max}^{KBr}$ cm$^{-1}$: 3410 (OH, NH), 1780 (CO of $\beta$-lactam), 1700 (CO of ester), 1660 (CO of amide).

NMR (CDCl$_3$)$\delta$: 1.41 (3H, d, J=6.4 Hz, —CHOH-C$\underline{H}_3$), 1.96 (3H, s, —CO—C$\underline{H}_3$), 2.83–3.91 (7H, m, C—4H, C—6H, —SCH$_2$CH$_2$NH—), 4.00–4.50 (2H, m, C-5$\underline{H}$, -C$\underline{H}$OH-), 5.21 (1H, d, J=14.0 Hz, —C$\underline{H}$H-Ar), 5.45 (1H, d, J=14.0 Hz, —CH$\underline{H}$-Ar), 7.60 (2H, d, J=8.41 Hz, —CH$_2$-Ar), 8.17 (2H, d, d, J=8.4 Hz, —CH$_2$-Ar).

Mass (m/e): 363 (M+-CH$_3$CHOH.CH=C=O).

EXAMPLE 9

Production of the sulfoxide of PS-5.p-nitrobenzyl ester

PS-5-nitrobenzyl ester (240 mg) obtained by the method of Example 1 was dissolved in 25 ml of dry methylene chloride, and cooled to $-30°$ C. A solution of 104.9 mg of m-chloroperbenzoic acid in 12 ml of dry methylene chloride was added to the resulting solution with stirring and reacted at this temperature for 40 minutes. After the reaction, the reaction mixture was poured into a solution of 0.09 ml of triethylamine in 100 ml of ethyl acetate, which had previously been prepared and cooled with ice. The mixture was stirred for 5 minutes with ice cooling, and 100 ml of ethyl acetate was added. The mixture was transferred into a separating funnel, and washed four times with an ice-cooled phosphate buffer (0.1 M; pH 6.8). The solvent layer was dried over anhydrous sodium sulfate, and then benzene was added. The mixture was concentrated under reduced pressure to a volume of 1 ml. The concentrate was passed through a column of 18 g of silica gel (42 ml, 2.0×13.4 cm, the same silica gel as described hereinabove) wetted with benzene-acetone (1:1), and developed with about 50 ml of the same solvent. The resulting eluate contained 1.4 mg of the starting material. The eluate was further developed with about 60 ml of benzene-acetone (1:2), and then with 70 ml of benzene-acetone (1:3) to afford 211 mg (89%) of the captioned compound. In a silica gel TLC plate, this compound showed an Rf value of 0.36 with benzene-acetone (1:2).

$[\alpha]_D^{21}$ +18.0° (c 1.00, CHCl$_3$).

UV$\lambda_{max}^{CHCl3}$ nm($\epsilon$): 267 (13100), 310 (7800).

IR$\lambda_{max}^{CHCl3}$ cm$^{-1}$: 3460 (N$\underline{H}$CO), 1785 (CO of $\beta$-lactam), 1720 (CO of ester), 1680 (NHCO).

NMR (CDCl$_3$)$\delta$: 1.08 (3H, t, J=7.0 Hz, CH$_2$C$\underline{H}_3$), 1.84 (2H, m, C$\underline{H}_2$CH$_3$), 2.00 (3H, s NHCOC$\underline{H}_3$), 2.90–3.92 (7H, m, 3XCH$_2$, CH), 3.92–4.23 (1H, m, CH), 5.22 (1H, d, J=14.0 Hz, ArC$\underline{H}$H), 5.48 (1H, d, J=14.0 Hz, ArCH$\underline{H}$), 6.40 (1H, brs, N$\underline{H}$), 7.53–7.72 (2H, d, J=9.0 Hz, Ar$\underline{H}$), 8.12–8.28 (2H, d, J=9.0 Hz, ArH).

Mass (m/e): 449 (M+) (FD Mass).

The compounds shown in Examples 10 to 14 below were obtained in a similar manner to Example 9 using the corresponding compounds obtained in Examples 2 to 5.

EXAMPLE 10

PS-5.-benzyl ester, sulfoxide $[\alpha]_D^{21}$ −43.96 (c, 1.00, MeOH).

UV$\lambda_{max}^{MeOH}$ nm($\epsilon$): 307 (4400).

IR$\lambda_{max}^{CHCl3}$ cm$^{-1}$: 3400 (N$\underline{H}$CO), 1790 (CO of $\beta$-lactam), 1710 (CO of ester), 1670 (NHCO).

NMR (CDCl$_3$)$\delta$: 1.04 (3H, t, J=7.04 Hz, CH$_2$C$\underline{H}_3$), 1.86 (2H, m, C$\underline{H}_2$CH$_3$), 1.94 (3H, s, COC$\underline{H}_3$), 2.90–3.84 (7H, m, 3XCH$_2$, C$\underline{H}$), 4.12 (1H, m, C-5$\underline{H}$), 5.26 (2H, s, ArCH$_2$), 6.40 (1H, m, NH), 7.36 (5H, s, Ar$\underline{H}$).

Mass (m/e): 404 (M+).

EXAMPLE 11

Sulfoxide of PS-5.benzhydryl ester $[\alpha]_D^{21}$ −64.04° (c 0.28, CHCl$_3$).

UV$\lambda_{max}^{MeOH}$ nm($\epsilon$): 308 (5600).

IR$\lambda_{max}^{CHCl3}$ cm$^{-1}$: 3450 (NHCO-), 1790 (CO of $\beta$-lactam), 1710 (CO of ester), 1670 (NHCO).

NMR (CDCl$_3$)$\delta$: 1.08 (3H, t, J=8 Hz, —CH$_2$—CH$_3$), 1.92 (3H, s, —NHCOC$\underline{H}_3$), 4.08 (1H, dt, J=9 Hz, J=3

Hz, C-5H), 6.34 (1H, br, N$\underline{H}$), 6.87 (1H, s, -C$\underline{H}$Ar$_2$), 7.32 (10H, distorted, s, —CHAr$_2$).

Mass (m/e): 480 (M+).

EXAMPLE 12

Sulfoxide of PS-5.methyl ester $[\alpha]_D^{21}=74.23°$ (c 0.25, CHCl$_3$).
UV$\lambda_{max}^{MeOH}$ nm($\epsilon$): 303 (5200).
IR$\lambda_{max}^{CHCl3}$ cm$^{-1}$: 3450 (N$\underline{H}$CO), 1790 (CO of $\beta$-lactam), 1720 (CO of ester), 1670 (NHC0).
NMR (CDCl$_3$)$\delta$: 1.07 (3H, t, J=8 Hz, —CH$_2$—C$\underline{H}_3$), 1.70-2.00 (2H, m, —C$\underline{H}_2$—CH$_3$), 2.00 (3H, s, —NHCOCH$_3$), 2.90:-3.90 (7H, m, 3X-C$\underline{H}_2$—, —CH—), 3.89 (3H, s, —CO$_2$CH$_3$), 4.00-4.20 (1H, m, C-5H), 6.60 (1H, brs, —NH).

Mass (m/e): 328 (M+) (FD Mass).

EXAMPLE 13

Sulfoxide of PS-6.p-nitrobenzyl ester

UV$\lambda_{max}^{CHCl3}$ nm($\epsilon$): 267 (13000), 310 (7800)
IR$\lambda_{max}^{CHCl3}$ cm$^{-1}$: 1792 (CO of $\beta$-lactam), 1720 (ester).
NMR (CDCl$_3$)$\delta$:

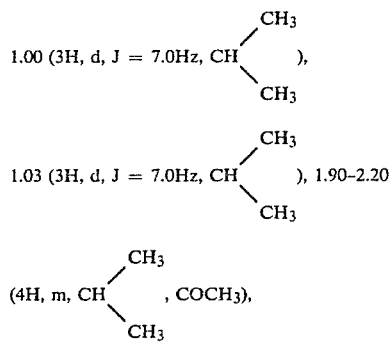

2.90-4.25 (8H, m, C-4H, C-5H, C-6H, 2×CH$_2$). 5.22 (1H, d, J=14.0 Hz, ArC$\underline{H}$H), 5.44 (1H, d, J=14.0 Hz, ArCH$\underline{H}$), 6.45 (1H, m, NH), 7.56 (2H, d, J=9.0 Hz, ArH), 8.18 (2H, d, J=9.0 Hz, ArH).

EXAMPLE 14

Sulfoxide of PS-6.benzyl ester

UV$\lambda_{max}^{MeOH}$: 307 nm.
IR$\lambda_{max}^{CHCl3}$ cm$^{-1}$: 3400 (—NHCO), 1780 (CO of $\beta$-lactam), 1710 (CO of ester), 1670 (NHCO).
NMR (CDCl$_3$)$\delta$: 1.07 (6H, t, J=7 Hz, —CH(C$\underline{H}_3$)$_2$), 1.98 (3H, s, —NHCOC$\underline{H}_3$), 4.12 (1H, m., C-5H), 5.29 (2H, s, —C$\underline{H}_2$-AR), 6.47 (1H, brs, —N$\underline{H}$), 7.37 (5H, s,-like, Ar$\underline{H}$).

Mass (m/e): 418 (M+) (FD Mass).

EXAMPLE 15

Production of p-nitrobenzyl 5,6-trans-3-(2-acetamidoethylsulfinyl)-6-(1-hydroxyethyl)-7-oxo-1-azabicyclo[3.2.0]hept-2-ene-2-carboxylate (the sulfoxide of PS-3A.p-nitrobenzyl ester)

PS-3A-p-nitrobenzyl ester (10.1 mg) was dissolved in 20 ml of dry tetrahydrofuran, and the solution was cooled to −25° C. With stirring, a solution of 5.2 mg of m-chloroperbenzoic acid in 0.2 ml of dry dichloromethane was added dropwise in a stream of nitrogen. The mixture was stirred at this temperature for 1 hour. The reaction mixture was diluted with 40 ml of ethyl acetate, washed with a phosphate buffer (0.1 M; pH 6.8) and then with a saturated aqueous solution of sodium bicarbonate, and dried over anhydrous sodium sulfate. The evaporation residue was adsorbed to a silica gel column (5 g, 1.1×15 cm, the same as the silica gel described hereinabove), and eluted with acetone to afford 2.6 mg of the captioned compound.

UV$\lambda_{max}^{THF}$ nm($\epsilon$): 323 sh, (3300), 270 (8900).
IR$\lambda_{max}^{CHCl3}$ cm$^1$: 3450 (—OH, NH), 1790 (CO of $\beta$-lactam), 1720 (CO of ester), 1680 (CO of amide).
NMR (CDCl$_3$)$\delta$: 1.41 (3H, d, J=6.0 Hz, —CHOH-C$\underline{H}_3$), 1.97 (3H, S, —CO-C$\underline{H}_3$), 3.00-3.90 (7H, m, C-6H, C-4H$_2$, S-C$\underline{H}_2$—CH$_2$NH), 4.00-4.55 (2H, m, C-5$\underline{H}$, C-7H), 5.25 (1H, d, J=14 Hz, C$\underline{H}$H-Ar), 5.42 (1H, d, J=14 Hz, CH$\underline{H}$-Ar), 6.10-6.50 (1H, m, -NH—), 7.58 (2H, d, J=9.0 Hz, —ArH), 8.19 (2H, d, J=9.0 Hz, —ArH).

EXAMPLE 16

Production of p-nitrobenzyl 5,6-cis-3-(2-acetamidoethylsulfinyl)-6-(1-hydroxyethyl)-7-oxo-1-azabicyclo[3.2.0]hept-2-ene-2-carboxylate (the sulfoxide of PS-3B.p-nitrobenzyl ester)

Example 15 was repeated except that the PS-3B.p-nitrobenzyl ester was used as a starting material instead of PS-3A.-p-nitrobenzyl ester.

UV$\lambda_{max}^{THF}$ nm($\epsilon$): 324 sh, (4500), 270 (14700).
IR$\lambda_{max}^{CHCl3}$ cm$^{-1}$: 3380 (—OH, NH), 1780 (CO of $\beta$-lactam), 1710 (CO of ester), 1665 (CO of amide).
NMR (CDCl$_3$) $\delta$: 1.42 (3H, d, J=6.0 Hz, CHOH-CH$_3$), 1.96 (3H, S, CO—CH$_3$), 2.90-3.95 (7H, m, C-6H, C-4H$_2$, SCH$_2$CH$_2$N), 5.24 (1H, d, J=14.0 Hz, CHHAr), 5.41 (1H, d, J=14.0 Hz, CHHAr), 7.58 (2H, d, J=8.4 Hz, ArH), 8.19 (2H, d, J=8.4 Hz, ArH).

EXAMPLE 17 p-Nitrobenzyl 3-(4-pyridylthio)-6-ethyl-7-oxo-1-azabicyclo[3.2.0]hept-2-ene-2-carboxylate 150 mg (0.372 mmol) of the sulfoxide of PS-5.p-nitrobenzyl ester was dissolved in 40 ml of dry dimethylformamide, and the solution was cooled to −50° C. With stirring, a solution of 64.5 g (0.483 mmol) of a sodium salt of 4-pyridyl mercaptan in 10 ml of dry dimethylformamide was added to the resulting solution, and reacted for 40 minutes. The reaction mixture was poured into 150 ml of benzene, and washed three times with 70 ml of a 0.1 M phospate buffer (pH 8.5). The organic layer was dried over anhydrous sodium sulfate, and benzene was distilled off under reduced pressure to afford a pale yellow oily product.

The product was applied to a column (1.0×15 cm) packed with silica gel using benzene, and developed with a benzene-acetone (5:1 v/v) solvent. The desired product was searched from the resulting fractions by means of thin layer chromatography. Fractions containing the desired product were collected, and concentrated under reduced pressure to afford 47 mg of the desired product (29.7% yield).

$[\alpha]_D^{22}+18.4°$ (c 1.00, THF).
UV$\lambda_{max}^{THF}$ nm($\epsilon$): 322 (7900), 267 (8700).
IR$\nu_{max}^{CHCl3}$ cm$^{-1}$: 1785 (CO of $\beta$-lactam), 1720 (CO of ester).
NMR (CDCl$_3$)$\delta$: 1.10 (3H, t, J=7.5 Hz, CH$_2$C$\underline{H}_3$), 1.64-2.04 (2H, m, C$\underline{H}_2$CH$_3$), 2.60-3.24 (3H, m, C-4 H, C 6 H), 3.92 (1H, dt, J=9 Hz, J=3 Hz, C-5 H), 5.30 (1H, d, J=14 Hz, ArC$\underline{H}$.H), 5.58 (1H, d, J=14 Hz, ArCH.$\underline{H}$), 7.40 (2H, dd, J=6 Hz, J=2 Hz, PyH), 7.68

(2H, d, J=9 Hz, ArH), 8.24 (2H, d, J=9 Hz, ArH), 8.60 (2H, dd, J=6 Hz, J=2 Hz, PyH).

Mass (m/e): 425 (M+), 355 (M+-EtCH=C=O).

The compounds shown in Examples 18 to 25 below were obtained in a similar manner to Example 17.

EXAMPLE 18

Benzyl 3-(4-pyridylthio)-6-ethyl-7-oxo-1-azabicyclo[3.2.0]hept-2-ene-2-carboxylate UV$\lambda_{max}^{THF}$ nm($\epsilon$): 322 (8100).

IR$\nu_{max}^{CHCl_3}$ cm$^{-1}$: 1785 (CO of $\beta$-lactam), 1720 (CO of ester).

NMR (CDCl$_3$)$\delta$: 1.07 (3H, t, J=7.5 Hz, CH$_2$C$\underline{H_3}$), 1.60–2.00 (2H, m, C$\underline{H_2}$CH$_3$), 2.50–3.20 (3H, m, C-4 H, C-6 H), 3.88 (1H, dt, J=9 Hz, J=3 Hz, C-5 H), 5.36 (1H, d, J=12 Hz, ArC$\underline{H}$.H), 5.49 (1H, d, J=12 Hz, ArCH.$\underline{H}$), 7.30–7.44 (2H, m, PyH), 8.50–8.70 (2H, m, PyH).

Mass (m/e): 380 (M+), 310 (M+-EtCH=C—O).

EXAMPLE 19 p-Nitrobenzyl 3-(4-pyridylthio)-6-isopropyl-7-oxo-1-azabicyclo[3.2.0]hept-2-ene-2-carboxylate UV$\lambda_{max}^{THF}$ nm($\epsilon$): 322 (8000), 267 (8800)

IR$\nu_{max}^{CHCl_3}$ cm$^{-1}$: 1785 (CO of $\beta$-lactam), 1720 (CO of ester).

NMR (CDCl$_3$)$\delta$:

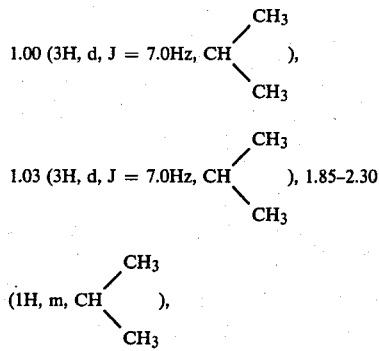

2.60–3.30 (3H, m, C-4H, C-6H), 3.95 (1H, dt, J=9.0 Hz, J=3.0 Hz, C-5H), 5.28 (1H, d, J=14.0 Hz, ArCH.$\underline{H}$), 5.58 (1H, d, J=14.0 Hz, ArCH.$\underline{H}$), 7.41 (2H, dd, J=6.0 Hz, J=2.0 Hz, PyH), 7.68 (2H, d, J=9.0 Hz, ArH), 8.25 (2H, d, J=9.0 Hz, ArH), 8.60 (2H, dd, J=6.0 Hz, J=2.0 Hz, PyH).

EXAMPLE 20

N-Nitrobenzyl 5,6-trans-3-(4-pyridylthio)-6-(1-hydroxyethyl)-7-oxo-1-azabicyclo[3.2.0]hept-2-ene-2-carboxylate UV$\lambda_{max}^{THF}$ nm($\epsilon$): 322 (8500), 267 (9200).

IR$\nu_{max}^{CHCl_3}$ cm$^{-1}$: 1785 (CO of $\beta$-lactam), 1720 (CO of ester).

NMR (CDCl$_3$)$\delta$: 1.35 (3H, d, J=7.0 Hz, CH-C$\underline{H_3}$), 2.60–3.50 (3H, m, C-4H, C-6H), 3.80–4.35 (2H, m, C-5H, HOC$\underline{H}$-CH$_3$), 5.28 (1H, d, J=14.0 Hz, ArC$\underline{H}$.H), 5.54 (1H, d, J=14.0 Hz, ArCH.$\underline{H}$), 7.39 (2H, dd, J=6.0 Hz, J=2.0 Hz, PyH), 7.68 (2H, d, J=9.0 Hz, Ar$\underline{H}$), 8.24 (2H, d, J=9.0 Hz, ArH), 8.60 (2H, dd, J=6.0 Hz, J=2.0 Hz, Py$\underline{H}$).

EXAMPLE 21 p-Nitrobenzyl 5,6-cis-3-(4-pyridylthio)-6-(1-hydroxyethyl)-7-oxo-1-azabicyclo[3.2.0]hept-2-ene-2-carboxylate:

UV$\lambda_{max}^{THF}$ nm($\epsilon$): 322 (8300), 267 (9100).

IR$\nu_{max}^{CHCl_3}$ cm$^{-1}$: 1785 (CO of $\beta$-lactam), 1720 (ester).

NMR (CDCl$_3$): 1.37 (3H, d, J=7.0 Hz, CHC$\underline{H_3}$), 2.60–4.40 (5H, m, C-4H, C-5H, C-6H, HOCHCH$_3$), 5.28 (1H, d, J=14.0 Hz, ArC$\underline{HH}$), 5.56 (1H, d, J=14.0 Hz, ArCH$\underline{H}$), 7.38 (2H, dd, J=6.0 Hz, J=2.0 Hz, PyH), 7.66 (2H, d, J=9.0 Hz, ArH), 8.24 (2H, d, J=9.0 Hz, ArH), 8.62 (2H, dd, J=6.0 Hz, J=2.0 Hz, PyH).

EXAMPLE 22 p-Nitrobenzyl 3-(2-pyrydylthio)-6-ethyl-7-oxo-1-azabicyclo[3.2.0]hept-2-ene-2-carboxylate $[\alpha]_D^{22}$+16.2° (c 1.00, THF).

IR$\nu_{max}^{CHCl_3}$ cm$^{-1}$: 1780 (CO of $\beta$-lactam), 1710 (CO of ester).

UV$\lambda_{max}^{THE}$ nm($\epsilon$): 325 (16900), 269 (12100).

NMR (CDCl$_3$)$\delta$: 1.00 (3H, t, J=7 Hz, CH$_2$C$\underline{H_3}$), 1.60–2.10 (2H, m, C$\underline{H_2}$CH$_3$), 2.92 (1H, dd, J=18 Hz, J=9 Hz, C-4H), 3.22 (1H, dd, J=18 Hz, J=9 Hz, C-4H), 3.07 (1H, dt, J=7 Hz, J=3 Hz, C-6H), 3.92 (1H, dt, J=9 Hz, J=3 Hz, C-5H), 5.26 (1H, dd, J=14 Hz, ArC$\underline{H}$H), 5.53 (1H, dd, J=14 Hz, ArCH$\underline{H}$), 7.40–7.80 (3H, m, PyH), 7.63 (2H, d, J=8 Hz, ArH), 8.20 (2H, d, J=8 Hz, ArH), 8.58 (1H, dd, J=5 Hz, J=2 Hz, PyH).

Mass (m/e): 425 (M+), 355 (M+—EtCH=C=O).

EXAMPLE 23 p-Nitrobenzyl 3-(2-pyridylthio)-6-isopropyl-7-oxo-1-azabicyclo[3.2.0]hept-2-ene-2-carboxylate UV$\lambda_{max}^{THF}$ nm($\epsilon$): 325 (16500), 269 (11500).

IR$\nu_{max}^{CHCl_3}$ cm$^{-1}$: 1780 (CO of $\beta$-lactam), 1708 (CO of ester).

NMR (CDCl$_3$)$\delta$:

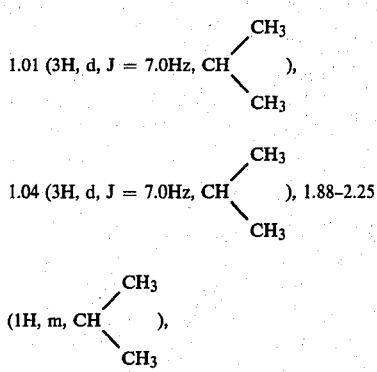

2.70–3.40 (3H, m, C-4H, C-6H), 3.94 (1H, dt, J=9.0 Hz, J=3.0 Hz, C-5H), 5.27 (1H, d, J=14.0 Hz, ArC$\underline{H}$H), 5.56 (1H, d, J=14.0 Hz, ArCH$\underline{H}$), 7.38–7.80 (3H, m, PyH), 7.62 (2H, d, J=8.0 Hz, ArH), 8.19 (2H, d, J=8.0 Hz, ArH), 8.59 (1H, dd, J=5.0 Hz, J=2.0 Hz, pyH).

EXAMPLE 24 p-Nitrobenzyl 5,6-trans-3-(2-pyridylthio)-6-(1-hydroxyethyl)-7-oxo-1-azabicyclo[3.2.0]hept-2-ene-2-carboxylate UV$\lambda_{max}^{THF}$ nm($\epsilon$): 325 (15900), 269 (11100).

IR$\nu_{max}^{CHCl_3}$ cm$^{-1}$: 1780 (CO of $\beta$-lactam), 1708 (ester).

NMR (CDCl$_3$)$\delta$: 1.36 (3H, d, J=7.0 Hz, CH-CH$_3$), 2.65–3.60 (3H, m, C-4H, C-6H), 3.80–4.40 (2H, m, C-5H, HOCHCH$_3$), 5.28 (1H, d, J=14.0 Hz, ArCHH), 5.56 (1H, d, J=14.0 Hz, ArCHH), 7.40–7.80 (5H, m, ArH, PyH), 8.20 (2H, d, J=9.0 Hz, ArH), 8.58 (1H, dd, J=5.0 Hz, J=2.0 Hz, PyH).

EXAMPLE 25 p-Nitrobenzyl 5,6-cis-3-(2-pyridylthio)-6-(1-hydroxyethyl)-7-oxo-1-azabicyclo[3.2.0]hept-2-ene-2-carboxylate UV$\lambda_{max}^{THF}$ nm($\epsilon$): 325 (15400), 269 (10800)

IR$\nu_{max}^{CHCl_3}$ cm$^{-1}$: 1780 (CO of $\beta$-lactam), 1708 (CO of ester).

NMR (CDCl$_3$)$\delta$: 1.37 (3H, d, J=7.0 Hz, CH—CH$_3$), 2.60–4.40 (5H, m, C-4H, C-5H, C-6H, HOCHCH$_3$), 5.26 (1H, d, J=14.0 Hz, ArCHH), 5.54 (1H, d, J=14.0 Hz, ArCHH), 7.40–7.80 (5H, m, PyH, ArH), 8.22 (2H, d, J=9.0 Hz, ArH), 8.60 (1H, dd, J=5.0 Hz, J=2.0 Hz, PyH).

EXAMPLE 26

Production of p-nitrobenzyl 3-(2-pyrimidinylthio)-6-ethyl-7-oxo-1-azabicyclo[3.2.0]hept-2-ene-2-carboxylate 100 mg (0.228 mmol) of the sulfoxide of PS-5. p-nitrobenzyl ester was dissolved in 15 ml. of dimethylformamide, and the solution was cooled to −35° C. With stirring, a solution of 33.5 mg (0.245 mmol) of a sodium salt of 2-mercaptopyrimidine in 6 ml of dry dimethylformamide was added to the resulting solution. The reaction was performed for 40 minutes. The reaction mixture was poured into 80 ml of benzene, and washed three times with 50 ml of a 0.1 M phosphate buffer (pH 8.4). The organic layer was dried over anhydrous sodium sulfate, and the solvent was distilled off under reduced pressure to afford a pale yellow oily product.

The product was applied to a column (1.2×18 cm) packed with 10 g of silica gel using benzene, and developed with a benzene-acetone (50:3 v/v) solvent. The fractions were screened by thin-layer chromatography, and fractions containing the desired product were collected. The solvent was removed by concentration under reduced pressure to afford 30 mg of the captioned product (yield 31.6%).

[$\alpha$]$_D^{22}$: +38.4° (c 0.47, THF).

UV$\lambda_{max}^{THF}$ nm($\epsilon$): 322 (9800), 268 (10300).

IR$\nu_{max}^{CHCl_3}$ cm$^{-1}$: 1780 (CO of $\beta$-lactam), 1715 (CO of ester).

NMR (CDCl$_3$)$\delta$: 1.08 (3H, t, J=7 Hz, CH$_2$CH$_3$), 1.68–2.00 (2H, m, CH$_2$CH$_3$), 3.00–4.10 (4H, m, C-4H, C-5H, C-6H), 5.28 (1H, d, J=14 Hz, ArCHH), 5.52 (1H, d, J=14 Hz, ArCHH), 7.04 (1H, t, J=6 Hz, C-5'H), 7.62 (2H. d. J=9 Hz, ArH), 8.20 (2H, d, J=9 Hz, ArH), 8.56 (2H, d, J=6 Hz, C-4'H, C-6'H).

Mass (m/e): 426 (M+), 356 (M+-EtCH=C=O).

The compounds shown in Examples 27 to 30 were obtained in a similar manner to Example 26.

EXAMPLE 27

Benzyl 3-(2-pyrimidinylthio)-6-ethyl-7-oxo-1-azabicyclo[3.2.0]hept-2-ene-2-carboxylate UV$\lambda_{max}^{THF}$ nm($\epsilon$): 321 (9900).

IR$\nu_{max}^{CHCl_3}$ cm$^{-1}$: 1780 (CO of $\beta$-lactam), 1715 (CO of ester).

NMR (CDCl$_3$)$\delta$: 1.04 (3H, t, J=7 Hz, CH$_2$CH$_3$), 1.63–1.95 (2H, m, CH$_2$CH$_3$), 3.00–4.10 (4H, m, C-4H, C-5H, C-6H), 5.34 (1H, d, J=13.5 Hz, ArCHH), 5.40 (1H, d, J=13.5 Hz, ArCHH), 7.10–8.00 (8H, m, PyH, ArH), 8.50–8.64 (1H, distored d, PyH).

Mass (m/e): 381 (M+), 311 (M+-EtCH=C=O).

EXAMPLE 28 p-Nitrobenzyl 3-(2-pyrimidinylthio)-6-isopropyl-7-oxo-1-azabicyclo[3.2.0]hept-2-ene-carboxylate UV$\lambda_{max}^{THF}$ nm($\epsilon$): 322 (10100), 267 (10500).

IR$\nu_{max}^{CHCl_3}$ cm$^{-1}$: 1780 (CO of $\beta$-lactam), 1715 (CO of ester).

NMR (CDCl$_3$)$\delta$:

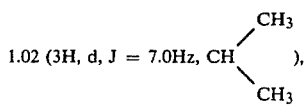

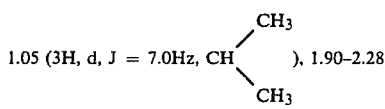

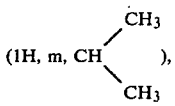

2.90–4.12 (4H, m, C-4H, C-5H, C-6H), 5.27 (1H, d, J=14 Hz, ArCHH), 5.53 (1H, d, J=14 Hz, ArCHH), 7.03 (1H, t, J=6.0 Hz, C-5'H), 7.60 (2H, d, J=9.0 Hz, ArH), 8.20 (2H, d, J=9.0 Hz, ArH), 8.54 (2H, d, J=6.0 Hz, C-4'H, C-6'H).

EXAMPLE 29 p-Nitrobenzyl 5,6-trans-3-(2-pyrimidinylthio)-6-(1-hydroxyethyl)-7-oxo-1-azsbicyclo[3.2.0]hept-2-ene-2-carboxylate UV$\lambda_{max}^{THF}$ nm($\epsilon$): 322 (10200), 268 (10700).

IR$\nu_{max}^{CHCl_3}$ cm$^{-1}$: 1780 (CO of $\beta$-lactam), 1715 (CO of ester).

NMR (CDCl$_3$)$\delta$: 1.37 (3H, d, J=7.0 Hz, CHCH$_3$), 2.80–4.40 (5H, m, C-4H, C-5H, C-6H, HOCHCH$_3$), 5.29 (1H, d, J=14.0 Hz, ArCHH), 5.50 (1H, d, J=14.0 Hz, ArCHH), 7.08 (1H, t, J=6.0 Hz, C-5'H), 7.64 (2H, d, J=9.0 Hz, ArH), 8.20 (2H, d, J=9.0 Hz, ArH), 8.55 (2H, d, J=6.0 Hz, C-4'H C-6'H).

EXAMPLE 30 p-Nitrobenzyl 5,6-cis-3-(2-pyrimidinylthio)-6-(1-hydroxyethyl)-7-oxo-1-azabicyclo[3.2.0]hept-2-ene-2-carboxylate UV$\lambda_{max}^{THF}$ nm($\epsilon$): 322 (10800), 268 (11200)

IR$\nu_{max}^{CHCl_3}$ cm$^{-1}$: 1780 (CO of $\beta$-lactam), 1715 (CO of ester)

NMR (CDCl$_3$)δ: 1.38 (3H, d, J=7.0 Hz, CH—C$\underline{H}_3$), 2.70–4.45 (5H, m, C-4H, C-5H, C-6H, HOC$\underline{H}$CH$_3$), 5.25 (1H, d, J=14.0 Hz, ArCH$\underline{H}$), 5.50 (1H, d, J=14.0 Hz, ArC$\underline{H}$H), 7.06 (1H, t, J=6.0 Hz, C-5'H), 7.62 (2H, d, J=9.0 Hz, ArH), 8.18 (2H, d, J=9.0 Hz, ArH), 8.52 (2H, d, J=6.0 Hz, C-4'H, C-6'H).

EXAMPLE 31

Production of p-nitrobenzyl 3-(phenylthio)-6-ethyl-7-oxo-1-azabicyclo[3.2.0]hept-2-ene-2-carboxylate 100 mg (0.228 mmol) of the sulfoxide of PS-5. p-nitrobenzyl ester was dissolved in 80 ml of dimethylformamide, and the solution was cooled to −50° C. With stirring, 37 microliters (0.267 mmol) of triethylamine was added to the resulting solution. Further, 27.4 microliters (0.267 mmol) of thiophenol was added, and the reaction was performed for 10 minutes. The reaction mixture was poured into 300 ml of benzene, and washed three times with 150 ml of a 0.1 M phosphate buffer (pH 6.8). The organic layer was dried over anhydrous sodium sulfate, and the benzene was distilled off under reduced pressure to afford a pale yellow oily product.

The product was applied to a column (1.2×20 cm) packed with 10 g of silica gel using benzene, and developed with a benzene-acetone (80:1 v/v) solvent. A part of the eluate was developed by thin-layer chromatography, and ultraviolet light having a wavelength of 360 nm was irradiated to search the desired product. Fractions containing the desired product were collected, and the solvent was distilled off under reduced pressure to afford 55.1 mg of the desired product (yield 65.2%).

[α]$_D^{22}$: +3.0° (c 1.00, THF).

UVλ$_{max}^{THF}$ nm(ε): 320 (11000), 271 (9100).

IRν$_{max}^{CHCl_3}$ cm$^{-1}$ 1780 (CO of β-lactam), 1710 (CO of ester).

NMR (CDCl$_3$)δ: 1.00 (3H, t, J=7.5 Hz, CH$_2$C$\underline{H}_3$), 1.6–1.90 (2H, m, C$\underline{H}_2$CH$_3$), 2.66 (2H, d, J=9 Hz, C-4H), 3.02 (1H, dt, J=9 Hz, J=3 Hz, C-6H), 3.82 (1H, dt, J=9 Hz, J=3 Hz, C-5H), 5.24, 5.54 (2H, each d, J=14 Hz, ArC$\underline{HH}$), 7.28–7.60 (5H, m, ArH), 7.68 (2H, d, J=9 Hz, ArH), 8.24 (2H, d, J=9 Hz, ArH).

Mass (m/e): 424 (M$^+$), 354 (M$^+$-EtCH=C=O).

The compounds shown in Examples 32 to 52 below were obtained in a similar manner to Example 31.

EXAMPLE 32 p-Nitrobenzyl 3-(p-nitrophenylthio)-6-ethyl-7-oxo-1-azabicyclo[3.2.0]hept-2-ene-2-carboxylate

[α]$_D^{22}$: +32.2° (c 1.00, THF).

UVλ$_{max}^{THF}$ nm(ε): 266 (17800), 310sh (12400).

IRν$_{max}^{CHCB}$ cm$^{-1}$: 1772 (CO of β-lactam), 1700 (CO of ester).

NMR (CDCl$_3$)δ: 1.02 (3H, t, J=7.5 Hz, CH$_2$C$\underline{H}_3$), 1.60–2.00 (2H, m, C$\underline{H}_2$CH$_3$), 2.78 (2H, d, J=9.0 Hz, C-4H), 3.08 (1H, m, C-6H), 3.92 (1H, dt, J=9 Hz, J=3 Hz, C-5H), 5.24 (1H, d, J=14 Hz, ArC$\underline{HH}$), 5.50 (1H,, d, J=14 Hz, ArC$\underline{H}$H), 7.64 (4H, d, J=9 Hz, ArH), 8.18 (4H, d, J=9 Hz, ArH).

Mass (m/e): 469 (M$^+$), 399 (M$^+$-Et-CH=C=O).

EXAMPLE 33 p-Nitrobenzyl 3-phenylthio-6-isopropyl-7-oxo-1-azabicyclo[3.2.0]hept-2-ene-2-carboxylate (PS-6.p-nitrobenzyl ester)

UVλ$_{max}^{THF}$ nm(ε): 320 (11500), 270 (9200).

IRν$_{max}^{CHCl_3}$ cm$^{-1}$: 1780 (CO of β-lactam), 1710 (CO of ester).

NMR (CDCl$_3$)δ:

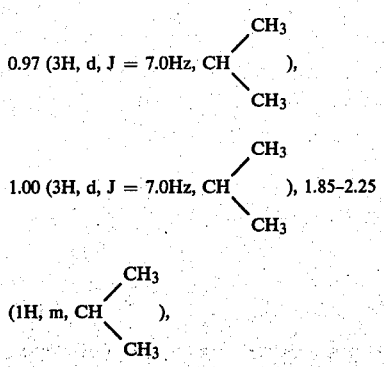

2.65 (2H, d, J=9.0 Hz, C-4H), 3.04 (1H, dd, J=3.0 Hz, J=9.0 Hz, C-6H), 3.83 (1H, dt, J=9.0 Hz, J=3.0 Hz, C-5H), 5.25 (1H, d, J=14.0 Hz, ArC$\underline{H}$H), 5.55 (1H, d, J=14.0 Hz, ArCH$\underline{H}$), 7.25–7.62 (5H, m, Ar$\underline{H}$), 7.67 (2H, d, J=9.0 Hz, ArH), 8.25 (2H, d, J=9.0 Hz, ArH).

EXAMPLE 34 p-Nitrobenzyl 5,6-trans-3-phenylthio-6-(1-hydroxyethyl)-7-oxo-1-azabicyclo[3.2.0]hept-2-ene-2-carboxylate UVλ$_{max}^{THF}$ nm(ε): 320 (11800), 270 (9800).

IRν$_{max}^{CHCl_3}$ cm$^{-1}$: 1770 (CO of β-lactam), 1700 (CO of ester),

NMR (CDCl$_3$)δ: 1.31 (3H, d, J=7.0 Hz, —CHOH—C$\underline{H}_3$), 2.68 (2H, d, J=9.0 Hz, C-4H), 3.18 (1H, dd, J=6.0 Hz, J=3.0 Hz, C-6H), 4.02 (1H, dt, J=9.5 Hz, J=3.0 Hz, C-5H), 4.12 (1H, m, —C$\underline{H}$OH—CH$_3$), 5.27 (1H, d, J=14.0 Hz, —C$\underline{H}$H-Ar), 5.56 (1H, d, J=14.0 Hz, —CH$\underline{H}$-Ar), 7.10–7.60 (5H, m, Ar$\underline{H}$), 7.67 (2H, d, J=9.0 Hz, ArH), 8.24 (2H, d, J=9.0 Hz, ArH).

The NMR spectrum chart is shown in FIG. 1 of the attached drawings.

EXAMPLE 35 p-Nitrobenzyl 5,6-cis-3-phenylthio-6-(1-hydroxyethyl)-7-oxo-1-azabicyclo[3.2.0]hept-2-ene-2-carboxylate UVλ$_{max}^{THF}$ nm(ε): 320 (11500), 270 (9500).

IRν$_{max}^{CHCl_3}$ cm$^{-1}$: 1775 (CO of β-lactam), 1710 (CO of ester).

NMR (CDCl$_3$)δ: 1.36 (3H, d, J=7.0 Hz, —CHOH—C$\underline{H}_3$), 2.55 (1H, dd, J=19.0 Hz, J=9.5 Hz, C-4H), 3.13 (1H, dd, J=19.0 Hz, J=9.5 Hz, C-4H), 3.52 (1H, dd, J=9.0 Hz, J=5.5 Hz, C-6H), 3.85–4.45 (2H, m, C-5H, HOC$\underline{H}$CH$_3$), 5.28 (1H, d, J=14.0 Hz, —C$\underline{H}$H-Ar), 5.56 (1H, d, J=14.0 Hz, —CH$\underline{H}$-Ar), 7.32–7.80 (7H, m, ArH), 8.22 (2H, d, J=9.0 Hz, ArH).

Figure 2:
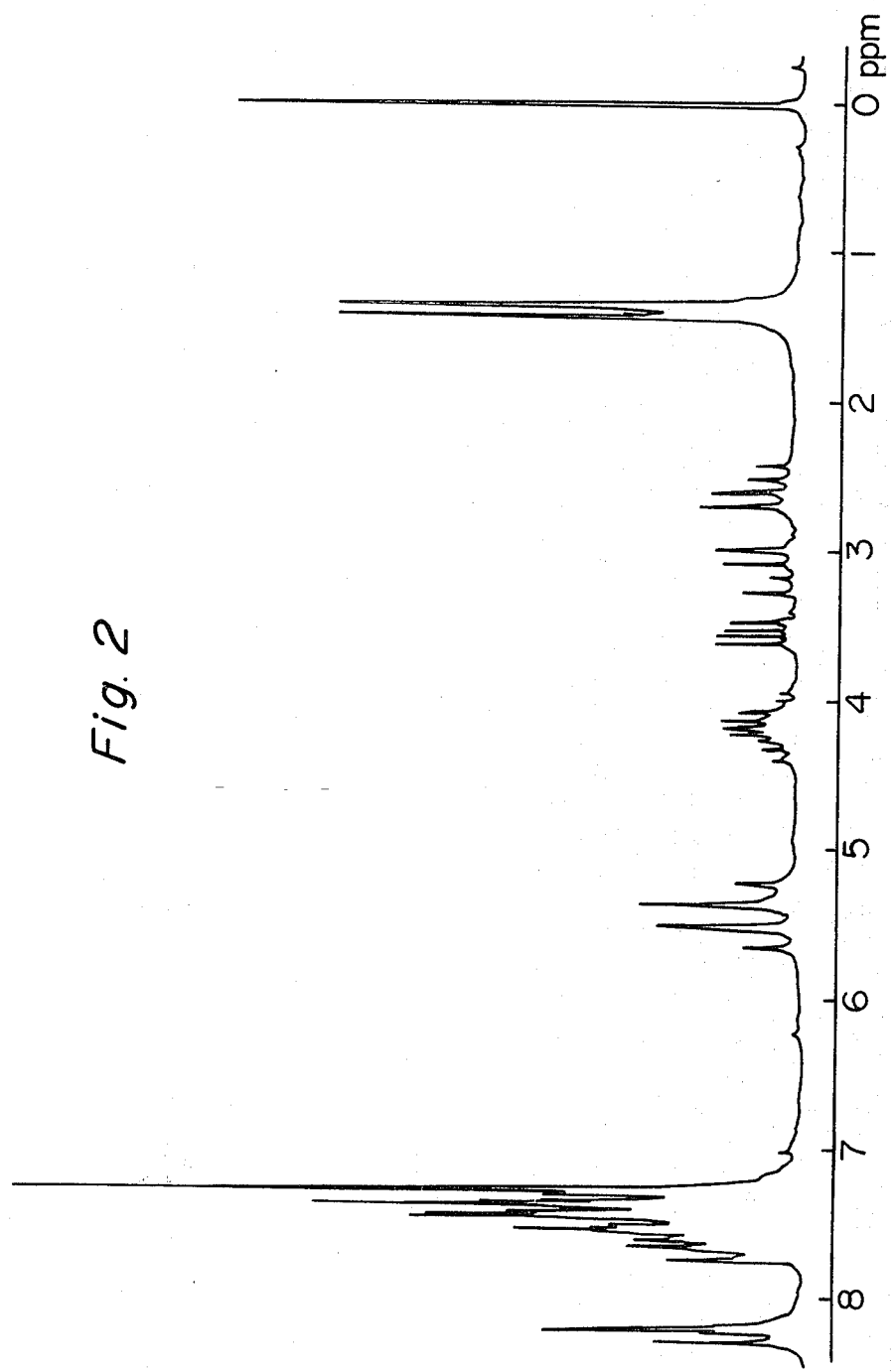

The NMR spectrum chart is shown in FIG. 2 of the attached drawings.

EXAMPLE 36 p-Nitrobenzyl 3-cyclohexylthio-6-ethyl-7-oxo-1-azabicyclo[3.2.0]hept-2-ene-2-carboxylate Rf: 0.43 (benzene:acetone=20:1).
[α]$_D^{22}$: +42.6° (c 1.00 THF).
UVλ$_{max}^{THF}$ nm(ε): 325 (15600), 270 (12800).
IRν$_{max}^{CHCl_3}$ cm$^{-1}$: 1770 (CO of β-lactam), 1695 (CO of ester).
NMR (CDCl$_3$)δ: 1.08 (3H, t, J=7.5 Hz, CH$_2$CH$_3$), 1.2–2.1 (12H, m, CH$_2$CH$_3$, Cyclohexyl CH$_2$), 2.8–3.2 (4H, m, C-4H, C-6H, SCH), 3.94 (1H, dt, J=9.0 Hz, J=3.0 Hz, C-4H), 5.18 (1H, d, J=14 Hz, ArCHH), 5.50 (1H, d, J=14 Hz, ArCHH), 7.62 (2H, d, J=9.0 Hz, ArH), 8.18 (2H, d, J=9.0 Hz, ArH).
Mass (m/e): 430 (M$^+$), 360 (M$^+$—Et-CH=C=O).

EXAMPLE 37 p-Nitrobenzyl 3-cyclohexylthio-6-isopropyl-7-oxo-1-azabicyclo[3.2.0]hept-2-ene-2-carboxylate UVλ$_{max}^{THF}$ nm(ε): 325 (15000), 270 (12100).
IRν$_{max}^{CHCl_3}$ cm$^{-1}$: 1770 (CO of β-lactam), 1695 (ester).
NMR (CDCl$_3$)δ:

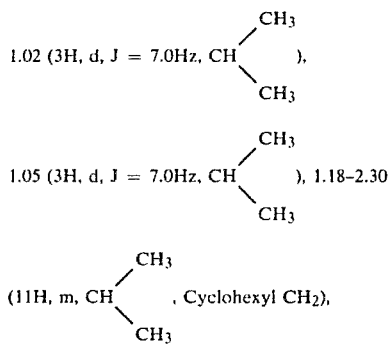

2.78–3.30 (4H, m, C-4H, C-6H, SCH), 3.96 (1H, dt, J=9.0 Hz, J=3.0 Hz, C-4H), 5.20 (1H, d, J=14.0 Hz, ArCHH), 5.48 (1H, d, J=14.0 Hz, ArCHH), 7.63 (2H, d, J=9.0 Hz, ArH), 8.20 (2H, d, J=9.0 Hz, ArH).

EXAMPLE 38 p-Nitrobenzyl 5,6-trans-3-cyclohexylthio-6-(1-hydroxyethyl)-7-oxo-1-azabicyclo[3.2.0]hept-2-ene-2-carboxylate UVλ$_{max}^{THF}$ nm(ε): 325 (14500), 270 (11600).
IRν$_{max}^{CHCl_3}$ cm$^{-1}$: 1770 (β-lactam), 1695 (ester).
NMR (CDCl$_3$)δ: 1.20–2.00 (13H, m, CH-CH$_3$, Cyclohexyl CH$_2$), 2.75–3.70 (4H, m, SCH, C-4H, C-6H), 3.80–4.38 (2H, m, C-5H, HOCH CH$_3$), 5.20 (1H, d, J=14.0 Hz, ArCHH), 5.50 (1H, d, J=14.0 Hz, ArCHH), 7.64 (2H, d, J=9.0 Hz, ArH), 8.18 (2H, d, J=9.0 Hz, ArH).

EXAMPLE 39 p-Nitrobenzyl 5,6-cis-3-cyclohexylthio-6-(1-hydroxyethyl)-7-oxo-1-azabicyclo[3.2.0]hept-2-ene-2-carboxylate UVλ$_{max}^{THF}$ nm(ε): 325 (14700), 270 (11700).
IRν$_{max}^{CHCl_3}$ cm$^{-1}$: 1770 (CO of β-lactam), 1695 (CO of ester).
NMR (CDCl$_3$)δ: 1.20–2.00 (13H, m, CH-CH$_3$, Cyclohexyl CH$_2$), 2.70–4.45 (6H, m, C-4H, C-5H, C-6H, SCH, HOCHCH$_3$), 5.20 (1H, d, J=14.0 Hz, ArCHH), 5.46 (1H, d, J=14.0 Hz, ArCHH), 7.60 (2H, d, J=9.0 Hz, ArH), 8.17 (2H, d, J=9.0 Hz, ArH).

EXAMPLE 40 p-Nitrobenzyl 3-n-butylthio-6-ethyl-7-oxo-1-azabicyclo[3.2.0]hept-2-ene-2-carboxylate UVλ$_{max}^{THF}$ nm(ε): 322.5 (11290).
(α)$_D^{21}$: +39.39° (c 0.917, THF).
IRν$_{max}^{CHCl_3}$ cm$^{-1}$: 1765 (CO of β-lactam), 1695 (CO of ester).
NMR (CDCl$_3$)δ: 0.80–1.18 (6H, m, 2X-CH$_2$CH$_3$), 1.20–2.00 (6H, m, 2X-CH$_2$-), 2.70–3.30 (5H, m, 2X-CH$_2$-, CH-), 3.94 (1H, dt, J=9 Hz, J=3 Hz, C-5H), 5.19 (1H, d, J=14 Hz, -CHHAr), 5.49 (1H, d, J=14 Hz, -CHHAr), 7.62 (2H, dd, J=9 Hz, J=2 Hz, ArH), 8.18 (2H, dd, J=9 Hz, J=2 Hz, ArH).
Mass (M/e): 404 (M$^+$), 334 (M$^+$-EtCH=C=O).

EXAMPLE 41 p-Nitrobenzyl 3-n-butylthio-6-isopropyl-7-oxo-1-azabicyclo[3.2.0]hept-2-ene-2-carboxylate UVλ$_{max}^{THF}$ nm(ε): 322 (11500), 270 (10100).
IRν$_{max}^{CHCl_3}$ cm$^{-1}$: 1770 (CO of β-lactam), 1695 (CO of ester).
NMR (CDCl$_3$)δ: 0.92 (3H, t, J=7.0 Hz,

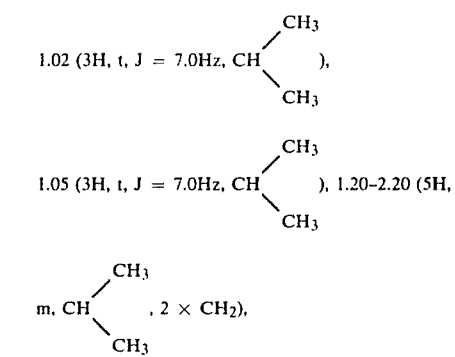

2.70–3.55 (5H, m, C-4H, C-6H, SCH$_2$), 3.95 (1H, d, J=9.0 Hz, J=3.0 Hz, C-5H), 5.20 (1H, d, J=14.0 Hz, ArCHH), 5.50 (1H, d, J=14.0 Hz, ArCHH), 7.64 (2H, d, J=9.0 Hz, ArH), 8.18 (2H, d, J=9.0 Hz, ArH).

EXAMPLE 42 p-Nitrobenzyl 5,6-trans-3-n-butylthio-6-(1-hydroxyethyl)-7-oxo-1-azabicyclo[3.2.0]hept-2-ene-2-carboxylate UVλ$_{max}^{THF}$ nm(ε): 322 (11000), 270 (9800).
IRν$_{max}^{CHCl_3}$: cm$^{-1}$: 1770 (CO of β-lactam), 1698 (CO of ester).
NMR (CDCl$_3$)δ: 0.93 (3H, t, J=7.0 Hz, CH$_2$CH$_2$CH$_2$CH$_3$), 1.20–2.00 (7H, m, 2×CH$_2$), CH-CH$_3$), 2.70–3.60 (5H, m, C-4H, SCH$_2$, C-6H), 3.80–4.40 (2H, m, C-5H, HOCHCH$_3$), 5.20 (1H, d, J=14.0 Hz, ArCHH), 5.50 (1H, d, J=14.0 Hz, ArCHH), 7.63 (2H, d, J=9.0 Hz, ArH), 8.20 (2H, d, J=9.0 Hz, ArH).

EXAMPLE 43 p-Nitrobenzyl 5,6-cis-3-n-butylthio-6-(1-hydroxyethyl)-7-oxo-1-azabicyclo[3.2.0]hept-2-ene-2-carboxylate UV$\lambda_{max}^{THF}$ nm($\epsilon$): 322 (11800), 270 (10500).

IR$\nu_{max}^{CHCl_3}$ cm$^{-1}$: 1770 (CO of $\beta$-lactam), 1695 (CO of ester).

NMR (CDCl$_3$)$\delta$: 0.92 (3H, t, J=7.0 Hz, CH$_2$CH$_2$CH$_2$C$\underline{H}_3$), 1.20-2.00 (7H, m, 2×CH$_2$, CHC$\underline{H}_3$), 2.60-3.65(5H, m, C-4H, C-6H, SCH$_2$), 3.80-4.40 (2H, m, C-5H, HOC$\underline{H}$CH$_3$), 5.18 (1H, d, J32 14.0 Hz, ArC$\underline{H}$H), 5.48 (1H, d, J=14.0 Hz, ArCH$\underline{H}$), 7.65 (2H, d, J=9.0 Hz, ArH), 8.20 (2H, d, J=9.0 Hz, ArH).

EXAMPLE 44 p-Nitrobenzyl 3-(2-hydroxyethylthio)-6-ethyl-7-oxo-1-azabicyclo[3.2.0]hept-2-ene-2-carboxylate IR$\nu_{max}^{CHCl_3}$ cm$^{-1}$: 3450 (OH), 1790 (CO of $\beta$-lactam), 1700 (CO of ester).

UV$\lambda_{max}^{THF}$nm ($\epsilon$): 320 (10400), 270 (10600).

$[\alpha]_D^{22}$: +33.2° (c 1.0, THF).

NMR (CDCl$_3$)$\delta$: 1.04 (3H, t, J=7.5 Hz, CH$_2$C$\underline{H}_3$), 1.75-2.05 (2H, m, C$\underline{H}_2$CH$_3$), 2.85-3.30 (5H, m, 2X$\overline{CH_2}$, CH), 3.70-4.10 (3H, m, C-5H, —CH$_2$OH), 5.18 (1H, d, J=14 Hz, ArC$\underline{H}$H), 5.49 (1H, d, J=14 Hz, ArCH$\underline{H}$), 7.80 (2H, d, J=9.0 Hz, ArH), 8.16 (2H, d, J=9.0 Hz, ArH).

Mass (m/e): 392 (M+), 322 (M+-EtCH=C=O), 304 (M+-EtCH=C=O-H$_2$O).

EXAMPLE 45 p-Nitrobenzyl 3-(2-hydroxyethylthio)-6-isopropyl-7-oxo-1-azabicyclo[3.2.0]hept-2-ene-2-carboxylate UV$\lambda_{max}^{THF}$ nm($\epsilon$): 320 (10500), 270 (10800).

IR$\nu_{max}^{CHCl_3}$ cm$^{-1}$: 1780 (CO of $\beta$-lactam), 1705 (CO of ester).

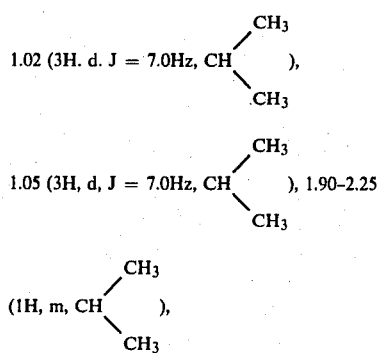

2.80-3.30 (5H, m, C-4H, S-CH$_2$, C-6H), 3.65-4.10 (3H, m, C-5H, CH$_2$OH), 5.20 (1H, d, J=14.0 Hz, ArC$\underline{H}$H), 5.50 (1H, d, J=14.0 Hz, ArCH$\underline{H}$), 7.78 (2H, d, J=9.0 Hz, ArH), 8.14 (2H, d, J=9.0 Hz, ArH).

EXAMPLE 46 p-Nitrobenzyl 5,6-trans-3-(2-hydroxyethylthio)-6-(1-hydroxyethyl)-7-oxo-1-1-azabicyclo[3.2.0]dept-2-ene-2-carboxylate UV$\lambda_{max}^{THF}$ nm($\epsilon$):m 320 (11000), 270 (11200).

IR$\nu_{max}^{CHCl_3}$ cm$^{-1}$: 1780 (CO of $\beta$-lactam), 1705 (CO of ester).

NMR (CDCl$_3$)$\delta$: 1.38 (3H, d, J=7.0 Hz, CH-C$\underline{H}_3$), 2.80-4.45 (8H, m, C-4H, C-5H, C-6H, 2×CH$_2$, HO-CH-CH$_3$), 5.18 (1H, d, J=14.0 Hz, ArC$\underline{H}$H), 5.45 (1H, d, J=14.0 Hz, ArCH$\underline{H}$), 7.58 (2H, d, J=9.0 Hz, ArH), 8.15 (2H, d, J=9.0 Hz, ArH).

EXAMPLE 47 p-Nitrobenzyl 5,6-cis-3-(2-hydroxyethylthio)-6-(1-hydroxyethyl)-7-oxo-1-azabicyclo[3.2.0]hept-2-ene-2-carboxylate UV$\lambda_{max}^{THF}$ nm($\epsilon$): 320 (11700), 270 (11800).

IR$\nu_{max}^{CHCl_3}$ cm$^{-1}$: 1778 (CO of $\beta$-lactam), 1705 (CO of ester).

NMR (CDCl$_3$)$\delta$: 1.40 (3H, d, J=7.0 Hz, CH—CH$_3$), 2.70-4.45 (9H, m, C-4H, C-5H, C-6H), 2×CH$_2$, HOC$\underline{H}$CH$_3$), 5.20 (1H, d, J=14.0 Hz, ArC$\underline{H}$H), 5.48 (1H, d, J=14.0 Hz, ArCH$\underline{H}$), 7.60 (2H, d, J=9.0 Hz, ArH), 8.18 (2H, d, J=9.0 Hz, ArH).

EXAMPLE 48 p-Nitrobenzyl 3-(2-ethoxyethylthio)-6-ethyl-7-oxo-1-azabicyclo[3.2.0]hept-2-ene-2-carboxylate IR$\nu_{max}^{CHCl_3}$ cm$^{-1}$: 1775 (CO of $\beta$-lactam), 1700 (CO of ester).

UV$\lambda_{max}^{THF}$ nm($\epsilon$): 320 (14100), 270 (12400).

$[\alpha]_D^{22}$: +45.7° (c 1.0, THF).

NMR (CDCl$_3$)$\delta$: 1.06 (3H, t, J=7.0 Hz, CH$_2$C$\underline{H}_3$), 1.18 (3H, t, J=7.0 Hz, CH$_2$C$\underline{H}_3$), 1.70-2.00 (2H, m, C$\underline{H}_2$CH$_3$), 2.90-3.70 (9H, m, C-6H, C-4H, 3X-CH$_2$), 3.91 (1H, dt, J=9 Hz, J=3 Hz, C-5H), 5.18 (1H, d, J=13 Hz, ArC$\underline{H}$H), 5.48 (1H, d, J=13 Hz, ArCH$\underline{H}$), 7.60 (2H, d, J=9 Hz, ArH), 8.15 (2H, d, J=9 Hz, ArH).

Mass (m/e): 420 (M+), 350 (M+-EtCH=C=O), 304 (M+-EtCH=C=O-EtOH).

EXAMPLE 49 p-Nitrobenzyl 3-(2-ethoxyethylthio)-6-isopropyl-7-oxo-1-azabicyclo[3.2.0]hept-2-ene-2-carboxylate UV$\lambda_{max}^{THF}$ nm($\epsilon$): 320 (13600), 269 (12000).

IR$\nu_{max}^{CHCl_3}$ cm$^{-1}$: 1775 (CO of $\beta$-lactam), 1700 (CO of ester).

NMR (CDCl$_3$)$\delta$:

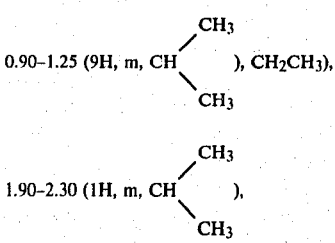

2.80-3.75 (9H, m, C-4H, C-6H, CH$_2$×3), 3.95 (1H, dt, J=9.0 Hz, J=3.0 Hz, C-5H), 5.20 (1H, d, J=14 Hz, ArC$\underline{H}$H), 5.48 (1H, d, J=14.0 Hz, ArCH$\underline{H}$), 7.62 (2H, d, J=9.0 Hz, ArH), 8.18 (2H, d, J=9.0 Hz, ArH).

EXAMPLE 50 p-Nitrobenzyl 5,6-trans-3-(2-ethoxyethylthio)-6-(1-hydroxyethyl)-7-oxo-1-azabicyclo[3.2.0]hept-2-ene-2-carboxylate UV$\lambda_{max}^{THF}$ nm($\epsilon$): 320 (13500), 270 (11800).

IR$\lambda_{max}^{CHCl_3}$ cm$^{-1}$: 1775 (CO of $\beta$-lactam), 1700 (CO of ester).

NMR (CDCl$_3$)$\delta$: 1.18 (3H, t, J=7.0 Hz, CH$_2$C$\underline{H_3}$), 1.38 (3H, d, J=7.0 Hz, CHC$\underline{H_3}$), 2.80–4.40 (11H, m, C-4H, C-5H, C-6H, HOC$\underline{H}$CH$_3$, 3×CH$_2$), 5.18 (1H, d, J=14.0 Hz, ArC$\underline{H}$H), 5.50 (1H, d, J=14.0 Hz, ArCH$\underline{H}$), 7.64 (2H, d, J=9.0 Hz, ArH), 8.20 (2H, d, J=9.0 Hz, ArH).

EXAMPLE 51 p-Nitrobenzyl 5,6-cis-3-(2-ethoxyethylthio)-6-(1-hydroxyethyl)-7-oxo-1-azabicyclo[3.2.0]hept-2-ene-2-carboxylate UV$\lambda_{max}^{THF}$ nm($\epsilon$): 320 (13000), 270 (11200).

IR$\nu_{max}^{CHCl_3}$ cm$^{-1}$: 1775 ($\beta$-lactam), 1705 (ester).

NMR (CDCl$_3$)$\delta$: 1.18 (3H, t, J=7.0 Hz, CH$_2$C$\underline{H_3}$), 1.38 (3H, d, J=7.0 Hz, CHC$\underline{H_3}$), 2.60–4.45 (11H, m, C-4H, C-5H, C-6H, 3×CH$_2$, HOC$\underline{H}$CH$_3$), 5.18 (1H, d, J=14.0 Hz, ArC$\underline{H}$H), 5.49 (1H, d, J=14.0 Hz, ArCH$\underline{H}$), 7.60 (2H, d, J=9.0 Hz, ArH), 8.18 (2H, d, J=9.0 Hz, ArH).

EXAMPLE 52 p-Nitrobenzyl 3-methylthio-6-ethyl-7-oxo-1-azabicyclo[3.2.0]hept-2-ene-2-carboxylate IR$\nu_{max}^{CHCl_3}$ cm$^{-1}$: 1778 (CO of $\beta$-lactam), 1702 (CO of ester), 1525, 1350 (NO$_2$).

UV$\lambda_{max}^{THF}$ nm($\epsilon$): 320 (9600), 269 (9400).

$[\alpha]_D^{25}$: +48.8° (c 0.5, THF)

Mass (m/e): 363 (M$^+$+1), 362 (M$^+$), 292 (M$^+$—CH$_3$CH$_2$CHCO).

NMR (CDCl$_3$)$\delta$: 1.04 (3H, t, J=7.0 Hz, CH$_2$C$\underline{H_3}$), 1.85 (2H, m, C$\underline{H_2}$CH$_3$), 2.36 (3H, S, S-CH$_3$), 3.12 (3H, m, C-4H, C-6H), 3.94 (1H, dt, J=9.0 Hz, J=3.0 Hz, C-5H). 5.20 (1H, d, J=15.0 Hz, ArC$\underline{H}$H), 5.50 (1H, d, J=15.0 Hz, ArCH$\underline{H}$), 7.60 (2H, d, J=8.0 Hz, ArH), 8.16 (2H, d, J=8.0 Hz, ArH).

EXAMPLE 53

Production of p-nitrobenzyl 3-(2-acetoxyethylthio)-6-ethyl-7-oxo-1-azabicyclo[3.2.0]hept-2-ene-2-carboxylate Triethylamine (13.3 microliters) was added to a solution in 2 ml of dichloromethane of 3.75 mg of the p-nitrobenzyl 3-(2-hydroxyethylthio)-6-ethyl-7-oxo-1-azabicyclo[3.2.0]hept-2-ene-2-carboxylate obtained in Example 44. Then, 6.8 microliters of acetyl chloride was added dropwise to the resulting solution at −10° C. with stirring. At the same temperature, the mixture was stirred for 10 minutes. The reaction mixture was diluted with 10 ml of benzene, and washed three times with 5 ml of a 0.1 M phosphate buffer (pH6.8). The organic layer was dried over anhydrous sodium sulfate, and the solvent was distilled off under reduced pressure to afford a yellow oily product.

The product was dissolved in benzene, and chromatographed on a column of Biobeads S-X3 (100 g, 3.2×75.0 cm) using benzene as a developing solvent. The fractions were analyzed by thin-layer chromatography, and fractions containing the desired product were collected. The solvent was distilled off under reduced pressure to afford 3.2 mg (77.1% yield) of a colorless oily product.

UV$\lambda_{max}^{THF}$ nm($\epsilon$): 317 (9600), 268 (9800),

IR[4 $_{max}^{CHCl_3}$ cm$^{-1}$: 1780 (CO of $\beta$-lactam), 1740 (O-COM$_e$), 1700 (CO of ester).

NMR (CDCl$_3$)$\delta$: 1.08 (3H, t, J=7 Hz, CH$_2$C$\underline{H_3}$), 1.70–2.20 (4H, m, C$\underline{H_2}$CH$_3$), 2.00 (3H, s, COC$\underline{H_3}$), 2.80–3.50 (5H, m, 2X-CH$_2$, CH), 3.98 (1H, dt, J=9.5 Hz, J=3 Hz, C 4.20 (2H, t, J=7.5 Hz, CH$_2$OCO—), 5.20 (1H, d, J=14 Hz, ArC$\underline{H}$H), 5.50 (1H, d, J=14 Hz, ArCH$\underline{H}$), 7.59 (2H, d, J=9.0 Hz, ArH), 8.15 (2H, d, J=9.0 Hz, ArH).

By treating the hydroxyethylthio derivatives obtained in Examples 45 to 47 in the same way as in Example 53, acetylated products corresponding to the starting materials were obtained as shown in Examples 54 to 56.

EXAMPLE 54 p-Nitrobenzyl 3-(2-acetoxyethylthio)-6-isopropyl-7-oxo-1-azabicyclo[3.2.0]hept-2-ene-2-carboxylate UV$\lambda_{max}^{THF}$ nm($\epsilon$): 317 (9800), 268 (10200).

IR$\nu_{max}^{CHCl_3}$ cm$^{-1}$: 1780 (CO of $\beta$-lactam), 1740 (OAc), 1700 (CO of ester).

NMR (CDCl$_3$)$\delta$:

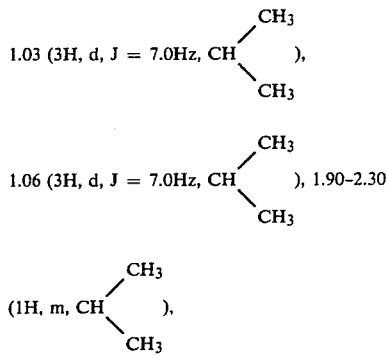

1.03 (3H, d, J = 7.0Hz, CH(CH$_3$)(CH$_3$)), 1.06 (3H, d, J = 7.0Hz, CH(CH$_3$)(CH$_3$)), 1.90–2.30

(1H, m, CH(CH$_3$)(CH$_3$)), 2.07 (3H, S, COCH$_3$), 2.70–3.50 (5H, m, SCH$_2$, C-4H, C-6H), 4.00 (1H, dt, J=9.5 Hz, J=3.0 Hz, C-5H), 4.20 (2H, t, J=7.5 Hz, CH$_2$OCO), 5.18 (1H, d, J=14.0 Hz, ArC$\underline{H}$H), 5.48 (1H, d, J=14.0 Hz, ArCH$\underline{H}$), 7.58 (2H, d, J=9.0 Hz, ArH), 8.14 (2H, d, J=9.0 Hz, ArH).

EXAMPLE 55 p-Nitrobenzyl 5,6-trans-3-(2-acetoxyethylthio)-6-(1-hydroxyethyl)-7-oxo-1-azabicyclo]3.2.0]hetp-2-ene-2-carboxylate UV$\lambda_{max}^{THF}$ nm($\epsilon$):317 (10200), 268 (10800).

IR$\nu_{max}^{CHCl_3}$ cm$^{-1}$: 17800 (CO of $\beta$-lactam), 1740 (OAc), 1700 (CO of ester).

NMR (CDCl$_3$)$\delta$: 1.37 (3H, d, J=7.0 Hz, CHC$\underline{H_3}$), 2.05 (3H, S, COCH$_3$), 2.80–4.45 (9H, m, C-4H, C-5H, C-6H, HOC$\underline{H}$-CH$_3$, 2×CH$_2$), 5.20 (1H, d, J=14.0 Hz, ArC$\underline{H}$H), 5.51 (1H, d, J=14.0 Hz, ArCH$\underline{H}$), 7.64 (2H, d, J=9.0 Hz, ArH), 8.20 (2H, d, J=9.0 Hz, ArH).

EXAMPLE 56 p-Nitrobenzyl 5,6-cis-3-(2-acetoxyethylthio)-6-(1-hydroxyethyl)-7-oxo-1-azabicyclo[3.2.0]hept-2-ene-2-carboxylate UV$\lambda_{max}^{THF}$ nm($\epsilon$): 317 (11100), 268 (11500).

IR$\nu_{max}^{CHCl_3}$ cm$^{-1}$: 1780 (CO of $\beta$-lactam), 1740 (OAc), 1700 (CO of ester).

NMR (CDCl$_3$)$\delta$: 1.38 (3H, d, J=7.0 Hz, CHC$\underline{H}_3$), 2.06 (3H, S, COCH$_3$), 2.65–4.50 (9H, m, C-4H, C-5H, 2×CH$_2$, HOC$\underline{H}$CH$_3$), 5.20 (1H, d, J=14.0 Hz, ArC$\underline{HH}$), 5.48 (1H, d, J=14.0 Hz, ArCH$\underline{H}$), 7.62 (2H, d, J=9.0 Hz, ArH), 8.18 (2H, d, J=9.0 Hz, ArH).

EXAMPLE 57

Production of 3-(4-pyridylthio)-6-ethyl-7-oxo-1-azabicyclo[3.2.0]hept-2-ene-2-carboxylic acid 54 mg of p-nitrobenzyl 3-(4-pyridylthio)-6-ethyl-7-oxo-1-azabicyclo[3.2.0]hept-2-ene-2-carboxylate obtained in Example 17 was dissolved in a mixture of 2 ml of dioxane and 2 ml of a 0.1 M phosphate buffer (pH 7.0). Then, 54 mg of platinum oxide was added, and the reaction was performed at room temperature for 4 hours in a Paar reducing apparatus (hydrogen pressure 4 kg/cm$^2$). The catalyst was removed by filtration. The filtrate and the wash liquid were combined and concentrated under reduced pressure to about $\frac{2}{3}$ of the original amount. To the resulting solution was added 2.5 g of sodium chloride, and further water was added to make the total amount 50 ml. The solution was charged on a column of Diaion HP-20AG (1.1×20 cm), and eluted with 300 ml in total of an aqueous solution of acetone having a concentration gradually varying from 0 to 30% by a concentration gradient method. The eluate was fractionated into 5 g fractions. The fractions were screened by high-velocity liquid chromatography, and fractions having an ultraviolet absorption at $\lambda_{max}$ 303 nm were collected, and lyophilized to afford 20.7 mg (yield 56.8%) of the captioned product.

UV$\lambda_{max}^{H_2O*}$ nm($\epsilon$): 303(8500).
*0.1 M phosphate buffer (pH 7.0)

NMR (D$_2$O)$\delta$: 1.00 (3H, t, J=7 Hz, CH$_2$C$\underline{H}_3$), 1.64–2.00 (2H, m, C$\underline{H}_2$CH$_3$), 2.92 (2H, d, J=9 Hz, C-4H), 3.34 (1H, dt, J=7.5 Hz, J=3 Hz, C-6H), 4.06 (1H, dt, J=9 Hz, J=3 Hz, C-5H), 7.50 (2H, dd, J=6 Hz, J=2 Hz, PyH), 8.30–8.60 (2H, m, PyH).

By the same reductive de-esterification method as in Example 57, the corresponding de-esterification products shown in Examples 58 to 60 were obtained from the ester compounds obtained in Examples 18 to 21.

EXAMPLE 58

3-(4-Pyridylthio)-6-isopropyl-7-oxo-1-azabicyclo[3.2.0]hept-2-ene-2-carboxylic acid UV$\lambda_{max}^{H_2O*}$ nm($\epsilon$): 303 (8200).
*0.1 M phosphate buffer (pH 7.0)
NMR (D$_2$O)$\delta$:

1.00 (3H, d, J = 7.0Hz, CH(CH$_3$)(CH$_3$)), 1.03 (3H, d, J = 7.0Hz, CH(CH$_3$)(CH$_3$)), 1.90–2.25

(1H, m, CH(CH$_3$)(CH$_3$)), 2.70–3.50 (3H, m, C-4H, C-6H), 4.08 (1H, dt, J=9.0 Hz, J=3.0 Hz, C-5H), 7.51 (2H, dd, J=6.0 Hz, J=2.5 Hz, PyH), 8.46 (2H, m, PyH).

EXAMPLE 59

5,6-trans-3-(4-Pyridylthio)-6-(1-hydroxyethyl)-7-oxo-1-azabicyclo[3.2.0]hept-2-ene-2-carboxylic acid UV$\lambda_{max}^{H_2O*}$ nm($\epsilon$): 303 (8800).
*0.1 M phosphate buffer (pH 7.0)

NMR (D$_2$O)$\delta$: 1.36 (3H, J=7.0 Hz, CHC$\underline{H}_3$), 2.75–3.65 (3H, m, C-4H, C-6H), 3.80–4.40 (2H, m, C-5H, HOC$\underline{H}$CH$_3$), 7.50 (2H, dd, J=6.0 Hz, J=2.5 Hz, PyH), 8.48 (2H, m, PyH).

EXAMPLE 60

5,6-cis-3-(4-Pyridylthio)-6-(1-hydroxyethyl)-7-oxo-1-azabicyclo[3.2.0]hept-2-ene-2-carboxylic acid UV$\lambda_{max}^{H_2O*}$ nm($\epsilon$): 303 (8100).
*0.1 M phosphate buffer (pH 7.0)

NMR (D$_2$O)$\delta$:1.38 (3H, d, J=7.0 Hz, CHC$\underline{H}_3$), 2.60–3.80 (3H, m, C-4H, C-6H), 3.90–4.45 (2H, m, C-5H, HOC$\underline{H}$CH$_3$), 7.52 (2H, dd, J=6.0 Hz, J=2.0 Hz, PyH), 8.46 (2H, m, PyH).

EXAMPLE 61

Production of 3-(2-pyrimidinylthio)-6-ethyl-7-oxo-1-azabicyclo[3.2.0]hept-2-ene-2-carboxylic acid 63.4 mg of p-nitrobenzyl 3-(2-pyrimidinylthio)6-ethyl-7-oxo-1-azabicyclo[3.2.0]hept-2-ene-2carboxylate obtained in Example 26 was dissolved in a mixture of 3.2 ml of dioxane and 1.2 ml of a 0.1 M phosphate buffer (pH 6.86). Then, 70 mg of platinum oxide was added, and the reaction was performed at room temperature for 4 hours in a Paar reducing apparatus (hydrogen pressure 4 kg/cm$^2$). The catalyst was removed by filtration. The filtrate and the wash liquid were combined, and after adjusting the pH of the mixture to 7.2, concentrated under reduced pressure to about $\frac{2}{3}$ of the initial amount. Sodium chloride (2 g) was added to the concentrated solution, and water was added to adjust the total amount to 70 ml. The resulting solution was applied to a column of Diaion HP-20AG (1.1×20 cm), and eluted with 300 ml in total of an aqueous solution of acetone with the concentration of acetone varying gradually from 0 to 50% (v/v) by a concentration gradient method. The fractions were screened by high-speed liquid chromatography, and fractions having an ultraviolet absorption at $\lambda_{max}$ 300 nm were collected and lyophilized to afford 16.8 mg of the desired product (yield 39%).

UV$\lambda_{max}^{H_2O*}$ nm($\epsilon$): 297 (6400).
*0.1 M phosphate buffer (pH 7.0)

NMR (D$_2$O)$\delta$: 1.02 (3H, t, J=7 Hz, CH$_2$C$\underline{H}_3$), 1.68–2.04 (2H, m, C$\underline{H}_2$CH$_3$), 2.84–3.52 (3H, m, C-4H, C-6H), 4.14 (1H, dt, J=9 Hz, J=3 Hz, C-5H), 7.35 (1H, t, J=6 Hz), C-5'H), 8.64 (2H, d, J=6 Hz, C-4'H, C-6'H).

As described in detail in Examples 57 and 61, other carboxylic acid esters obtained by this invention (for example, the compounds obtained in Examples 22, 25 and 31 to 52) can also be de-esterified by treating them in the same way as in Examples 57 or 61. The following Examples illustrate typical examples of the resulting compounds.

EXAMPLE 62

3-(2-Pyrimidinylthio)-6-isopropyl-7-oxo-1-azabicyclo[3.2.0]hept-2-ene-2-carboxylic acid UV$\lambda_{max}^{H2O*}$ nm($\epsilon$): 297 (6600).
*0.1 M phosphate buffer (pH 7.0)
NMR (D$_2$O)$\delta$:

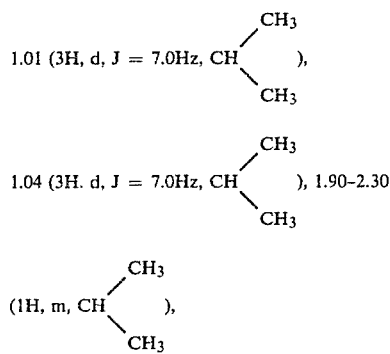

2.80–3.75 (3H, m, C-4H, C-6H), 4.15 (1H, dt, J=9.0 Hz, J=3.0 Hz, C-5H), 7.38 (1H, t, J=6.0 Hz, C-5'H), 8.63 (2H, d, J=6.0 Hz, C-4'H, C-6'H).

EXAMPLE 63

5,6-trans-3-(2-Pyrimidinylthio)-6-(1-hydroxyethyl)-7-oxo-1-azabicyclo[3.2.0]hept-2-ene-2-carboxylic acid UV$\lambda_{max}^{H2O*}$ nm($\epsilon$): 296 (6500).
*0.1 M phosphate buffer (pH 7.0)
NMR (D$_2$O)$\delta$: 1.38 (3H, d, J=7.0 Hz, CHC$\underline{H}_3$), 2.80–3.80 (3H, m, C-4H, C-6H), 3.95–4.50 (2H, m, C-5H, HOC$\underline{H}$CH$_3$), 7.37 (1H, t, J=6.0 Hz, C-5'H), 8.65 (2H, d, J=6.0 Hz, C-4'H, C-6'H).

EXAMPLE 64

5,6-cis-3-(2-Pyrimidinylthio)-6-(1-hydroxyethyl)-7-oxo-1-azabicyclo[3.2.0]hept-2-ene-2-carboxylic acid UV$\lambda_{max}^{H2O*}$ nm($\epsilon$): 297 (6800).
*0.1 M phosphate buffer (pH 7.0)
NMR (D$_2$O)$\delta$: 1.38 (3H, J=7.0 Hz, CHC$\underline{H}_3$), 2.60–3.85 (3H, m, C-4H, C-6H), 3.95–4.50 (2H, m, C-5H, HOC$\underline{H}$CH$_3$), 7.36 (1H, t, J=6.0 Hz, C-5'H), 8.63 (2H, d, J=6.0 Hz, C-4'H, C-6'H).

EXAMPLE 65

3-(2-Pyridylthio)-6-ethyl-7-oxo-1-azabicyclo-[3.2.0]hept-2-ene-2-carboxylic acid UV$\lambda_{max}^{H2O}$ nm($\epsilon$): 305 (12900).

NMR (CDCl$_3$)$\delta$: 0.99 (3H, t, J=7.5 Hz, CH$_2$C$\underline{H}_3$), 1.80 (2H, dq, J=7.5 Hz, C$\underline{H}_2$CH$_3$), 2.82 (2H, d, J=9.0 Hz, C-4H), 3.26 (1H, dt, J=7.5 Hz, J=3 Hz, C-6H), 3.98 (1H, dt, J=9.0 Hz, J=3 Hz, C-5H), 7.41, 7.62, 7.83 and 8.45 (1H, each m, ArH).

EXAMPLE 66

Sodium 3-(phenylthio)-6-ethyl-7-oxo-1-azabicyclo-[3.2.0]hept-2-ene-2-carboxylate UV$\lambda_{max}^{H2O*}$ nm($\epsilon$): 303 (10600).
*0.1 M phosphate buffer
NMR (D$_2$O)$\delta$: 0.96 (3H, t, J=7 Hz, CH$_2$C$\underline{H}_3$), 1.60–1.90 (2H, m, C$\underline{H}_2$CH$_3$), 2.40–2.90 (2H, m, C-4H), 3.15 (1H, dt, J=8 Hz, J=3 Hz, C-6H), 3.86 (1H, dt, J=9 Hz, J=3 Hz, C-5H), 7.35–7.65 (5H, m, ArH).

EXAMPLE 67

Sodium 3-cyclohexylthio-6-ethyl-7-oxo-1-azabicyclo[3.2.0.-]hept-2-ene-2-carboxylate UV$\lambda_{max}^{H2O*}$ nm($\epsilon$): 305 (6600).
*0.1 M phosphate buffer (pH 7.0)
NMR (D$_2$O)$\delta$: 1.04 (3H, t, J=7.5 Hz, CH$_2$C$\underline{H}_3$), 1.2–2.2 (12H, m, C$\underline{H}_2$CH$_3$, Cyclohexyl CH$_2$), 3.0–3.4 (4H, m, C-4H, C-6H, S-C$\underline{H}$), 4.02 (1H, dt, J=9 Hz, J=3 Hz, C-5H).

EXAMPLE 68

Sodium 3-n-butylthio-6-ethyl-7-oxo-1-azabicyclo[3.2.0]hept-2-ene-2-carboxylate

UV$\lambda_{max}^{H2O*}$ nm($\epsilon$): 302 (7550)
*0.1 M phosphate buffer (pH 7.0)
IR$\nu_{max}^{KBr}$ cm$^{-1}$: 1752 ($\beta$-lactam), 1600 (carboxylate).
NMR (D$_2$O)$\delta$: 0.93 (3H, t, —CH$_2$C$\underline{H}_3$), 1.04 (3H, t, —CH$_2$C$\underline{H}_3$), 1.20–2.00 (6H, m, 2X-C$\underline{H}_2$—), 2.50–3.50 (5H, m, —C$\underline{H}$—, 2X-C$\underline{H}_2$—), 4.02 (1H, dt, J=9.0 Hz, J=3.0 Hz, C-5H).

Representative formulations containing the compounds of formula (I-b) and/or the salt thereof can be prepared by the following procedures. (The compounds are shown by the above-mentioned Example numbers).

EXAMPLE A: CAPSULES

| Component | Per capsule |
|---|---|
| The compound of Example 57 | 100 mg |
| Lactose (J.P.) | a sufficient amount |
| Magnesium stearate | 1 mg |

The active compound and the diluents are mixed well in a mortar with a pestle to produce a uniform blend. Two hundred milligrams of the blend is filled in a No. 3 hard gelatin capsule covered with enteric-coating.

EXAMPLE B: TABLETS

| Component | Per tablet |
|---|---|
| The compound of Example 57 | 200 mg |
| Lactose (J.P.) | 120 mg |
| Corn starch | 175 mg |
| Magnesium stearate | 5 mg |
| | 500 mg |

In the above composition, the active component is blended with lactose and a half amount of corn starch. The mixture is granulated with a 10% starch and screened. The balance of corn starch and magnesium stearate are added and the mixture is compressed into tablets, approximately 1 cm in diameter, each weighing 500 mg. The tablets thus obtained are covered first with enteric-coating and then with sugar coating.

EXAMPLE C: LYO FORM FOR INJECTION

| Component | Per vial |
|---|---|
| The compound of Example 60 | 25 mg |
| Sterile distilled water for injection (J.P.) | 2 ml |

The active component is dissolved in sterile distilled water for injection, filtered and sterilized. The solution is sub-divided into sterile vials, and water is aseptically removed by lyophilization. The vials containing the sterile dry solid are aseptically sealed.

To restore for parenteral administration, 2 ml of sterile physiological saline (J.P.) is added to the content of a vial.

EXAMPLE D: TABLETS

| Component | Per tablet |
|---|---|
| The compound of Example 62 | 20 mg |
| Cephaloridine | 180 mg |
| Lactose (J.P.) | 120 mg |
| Corn starch | 175 mg |
| Magnesium stearate | 5 mg |
| | 500 mg |

The compound of Example 62 and cephaloridine are mixed with the other ingredients and compressed into tablets as described in Example B. The tablets are covered first with an enteric coating and then with a sugar coating.

EXAMPLE E: TABLETS

| Component | Per tablet |
|---|---|
| The compound of Example 65 | 10 mg |
| Aminobenzylpenicillin | 190 mg |
| Lactose (J.P.) | 120 mg |
| Corn starch | 175 mg |
| Magnesium stearate | 5 mg |
| | 500 mg |

By the same method as described in Example B, the tablets containing the compound of Example 65 and aminobenzylpenicillin are obtained.

EXAMPLE F: CAPSULES

| Component | Per capsule |
|---|---|
| The compound of Example 66 (sodium salt) | 100 mg |
| Lactose | a sufficient quantity |
| Magnesium stearate | 1 mg |

The active ingredient and diluents are well mixed to give a uniform blend. About 200 mg of each blend is filled in a No. 3 hard capsule and covered with enteric coating.

EXAMPLE G: TABLETS

| Component | Per tablet |
|---|---|
| The compound of Example 67 (sodium salt) | 200 mg |
| Lactose (J.P.) | 120 mg |
| Corn starch | 175 mg |
| Magnesium stearate | 5 mg |
| | 500 mg |

In the above example, the active ingredient is blended with lactose and a half amount of corn starch in the indicated ratio. The mixture is granulated with a 10% starch paste and sieved. Magnesium stearate and the balance of corn starch are added and the mixture is compressed into tablets of 1 cm in diameter, each weighing 500 mg. The tablets are covered first with an enteric-coating and then with a sugar-coating.

EXAMPLE H: LYO FORM FOR INJECTION

| Component | Per vial |
|---|---|
| The compound of Example 60 | 25 mg |
| Sterile distilled water for injection (J.P.) | 2 ml |

The active component is dissolved in sterile distilled water for injection and sterilized by filtration. The solution is subdivided in vials and aseptically freeze-dried. The vials containing the sterile dry solid are aseptically sealed.

On injection, 2 ml of sterile 70% N-($\beta$-hydroxyethyl)-lactamide is added to the content of a vial.

EXAMPLE I: TABLETS

| Component | Per tablet |
|---|---|
| The compound of Example 57 | 20 mg |
| Cephaloridine | 180 mg |
| Lactose (J.P.) | 120 mg |
| Corn starch | 175 mg |
| Magnesium stearate | 5 mg |

The compound of Example 57 and cephaloridine are mixed and then by the same method as described in Example C, compressed into tablets and coated.

EXAMPLE J: TABLETS

| Component | Per tablet |
|---|---|
| The compound of Example 59 | 20 mg |
| Aminobenzylpenicillin | 180 mg |
| Lactose (J.P.) | 120 mg |
| Corn starch | 175 mg |
| Magnesium stearate | 5 mg |
| | 500 mg |

The active ingredients (the compound of Example 59 and aminobenzylpenicillin) are mixed and processed by the same method as described in Example I.

What we claim is:

1. A process for producing a compound of the formula

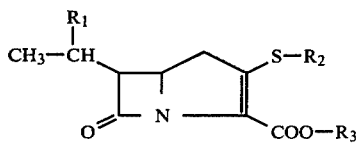 (I)

wherein
- $R_1$ represents hydrogen, methyl or hydroxyl,
- $R_2$ represents lower alkyl, hydroxy-lower alkyl, lower alkoxy-lower alkyl, lower alkanoyloxy-lower alkyl, cyclohexyl, phenyl, 2-pyridyl, 3-pyridyl, 4-pyridyl, 2-pyrimidinyl, 4-pyrimidinyl, 5-pyrimidinyl, 2-pyrrolyl, 3-pyrrolyl, 2-imidazolyl or 4-imidazolyl, and
- $R_3$ represents hydrogen, lower alkyl or lower alkyl substituted by 1 to 3 phenyl groups which may be substituted by a substituent selected from the group consisting of halogen, lower alkyl, lower alkoxy, lower haloalkyl, nitro and lower alkylsulfonyl, or its salt,
which comprises reacting a compound of the formula

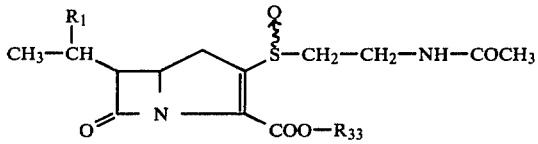 (II)

wherein
- $R_1$ is as defined above, and
- $R_{33}$ represents lower alkyl or lower alkyl substituted by 1 to 3 phenyl groups which may be substituted by a substituent selected from the group consisting of halogen, lower alkyl, lower alkoxy, lower haloalkyl, nitro and lower alkylsulfonyl, with a thiol compound of the formula $R_2SY$ wherein $R_2$ is as defined above, and Y represents hydrogen or an alkali metal, and, to produce a compound of formula (I) in which $R_3$ is hydrogen, hydrogenolyzing the resulting product, and if desired, converting the resulting product to its salt.

2. The process of claim 1 wherein $R_2$ in the thiol compound represents alkyl having 1 to 4 carbon atoms, hydroxyethyl, ethoxyethyl, acetyloxyethyl, cyclohexyl, phenyl, 2-pyridyl, 3-pyridyl, 4-pyridyl, 2-pyrimidinyl, 4-pyrimidinyl, 5-pyrimidinyl, 2-pyrrolyl, 3-pyrrolyl, 2-imidazolyl or 4-imidazolyl.

3. The process of claim 1 wherein $R_2$ in the thiol compound represents 2-pyridyl, 3-pyridyl, 4-pyridyl, 2-pyrimidinyl, 4-pyrimidinyl or 5-pyrimidinyl.

4. The process of claim 1 which produces a compound of the formula

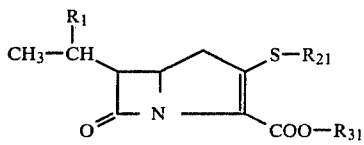 (I-a)

wherein
- $R_1$ is as defined in claim 29,
- $R_{21}$ represents alkyl having 1 to 4 carbon atoms, hydroxyethyl, ethoxyethyl, acetyloxyethyl, cyclohexyl, phenyl, 2-pyridyl, 3-pyridyl, 4-pyridyl, 2-pyrimidinyl, 4-pyrimidinyl, 5-pyrimidinyl, 2-pyrrolyl, 3-pyrrolyl, 2-imidazolyl or 4-imidazolyl, and
- $R_{31}$ represents hydrogen, methyl, benzyl, p-nitrobenzyl or benzhydryl.

5. The process of claim 1 which produces a compound of the formula

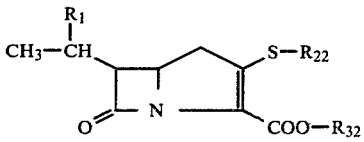 (I-b)

wherein
- $R_1$ is as defined in claim 29,
- $R_{22}$ represents phenyl, 2-pyridyl, 3-pyridyl, 4-pyridyl, 2-pyrimidinyl, 4-pyrimidinyl or 5-pyrimidinyl, and
- $R_{32}$ represents hydrogen or p-nitrobenzyl.

6. The process of claim 1 wherein the reaction is carried out at a temperature of not more than about $-20°$ C.

7. The process of claim 1 wherein the reaction is carried out in a solvent selected from the group consisting of N,N-dimethylformamide, tetrahydrofuran, dioxane, hexamethyl phosphoric triamide and glyme.

8. The process of claim 1 wherein the thiol compound is used in an amount of 1.1 to 1.5 moles per mole of the compound of the formula (II).

9. The process of claim 1 wherein $R_2$ in the thiol compound represents phenyl.

10. The process of claim 1 wherein $R_{33}$ in the compound of the formula (II) represents benzyl, phenethyl, benzhydryl, trityl, p-nitrobenzyl, o-nitrobenzyl, p-chlorobenzyl, o-chlorobenzyl, p-fluorobenzyl, p-bromobenzyl, p-methoxybenzyl, p-methylsulfonylbenzyl or p-trifluoromethylbenzyl.

11. The process of claim 1 wherein $R_{33}$ in the compound of the formula (II) represents methyl, benzyl, p-nitrobenzyl or benzhydryl.

12. The process of claim 1 wherein $R_{33}$ in the compound of the formula (II) represents p-nitrobenzyl.

* * * * *